US009152905B2

(12) United States Patent
Herold et al.

(10) Patent No.: US 9,152,905 B2
(45) Date of Patent: Oct. 6, 2015

(54) MICRODEVICE ARRAYS FORMED BY MAGNETIC ASSEMBLY

(75) Inventors: Christopher D. Herold, Del Mar, CA (US); David Rothwarf, La Jolla, CA (US); Bao Nguyen, San Diego, CA (US)

(73) Assignee: ARRAYOMICS, INC., San Diego, CA (US)

( * ) Notice: Subject to any disclaimer, the term of this patent is extended or adjusted under 35 U.S.C. 154(b) by 43 days.

(21) Appl. No.: 12/018,319

(22) Filed: Jan. 23, 2008

(65) Prior Publication Data
US 2008/0176762 A1 Jul. 24, 2008

Related U.S. Application Data

(60) Provisional application No. 60/886,370, filed on Jan. 24, 2007, provisional application No. 60/886,373, filed on Jan. 24, 2007.

(51) Int. Cl.
G01N 35/00 (2006.01)
G01N 35/04 (2006.01)
(Continued)

(52) U.S. Cl.
CPC ....... G06K 19/06187 (2013.01); B01J 19/0046 (2013.01); C40B 40/00 (2013.01);
(Continued)

(58) Field of Classification Search
CPC ............. B01J 2219/00549; B01J 2219/00563; B01J 2219/00655; B01J 2219/00497; B01J 19/0046; G01K 19/06187; G01N 33/54366; C40B 40/00; C40B 50/00

USPC ......... 204/545, 554, 557; 209/8, 28–40, 562, 209/609; 210/695, 222, 223; 422/99–101; 436/526; 435/6
See application file for complete search history.

(56) References Cited

U.S. PATENT DOCUMENTS 5,592,413 A 1/1997 Spitzer
6,569,382 B1 * 5/2003 Edman et al. ................ 422/68.1

(Continued)

FOREIGN PATENT DOCUMENTS

WO 98/23948 6/1998
WO 2003081526 10/2003

OTHER PUBLICATIONS

Liu et al., Arrays of magnetic nanoparticles patterned via "dip-pen" nanolithography, Feb. 5, Wiley-VCH, Adv. Mater. 2002, 14, No. 3, p. 231-234.*

(Continued)

Primary Examiner — Lyle Alexander
Assistant Examiner — Robert Eom
(74) Attorney, Agent, or Firm — Fish & Tsang, LLP

(57) ABSTRACT

Microdevices containing a predetermined preferential axis of magnetization are disposed in an array having discreet regions. Under influence of a magnetic field, the microdevices can have at least twelve discrete orientations, and can advantageously be flipped upside down in place. Microdevices can be coded in a manner that supports a coding space of at least $10^2$, $10^3$, $10^6$ or even $10^{10}$ or more choices, and can include one or more chemically reactive sites. The regions can be defined by long and short bars, in which microdevices span gaps between the longer bars, and the shorter bars measure less than 60% of such gaps. Preferred embodiments are also provided to produce microfabricated microdevices for magnetic assembly-based arraying.

22 Claims, 23 Drawing Sheets

(51) Int. Cl.
  *G06K 19/06* (2006.01)
  *B01J 19/00* (2006.01)
  *C40B 40/00* (2006.01)
  *C40B 50/00* (2006.01)
  *G01N 33/543* (2006.01)

(52) U.S. Cl.
  CPC ......... *C40B 50/00* (2013.01); *G01N 33/54326* (2013.01); *G01N 33/54366* (2013.01); *B01J 2219/00497* (2013.01); *B01J 2219/00549* (2013.01); *B01J 2219/00563* (2013.01); *B01J 2219/00655* (2013.01)

(56) References Cited

U.S. PATENT DOCUMENTS

| | | | |
|---|---|---|---|
| 6,858,184 B2* | 2/2005 | Pelrine et al. | 422/68.1 |
| 7,015,047 B2 | 3/2006 | Huang et al. | |
| 7,718,419 B2 | 5/2010 | Wu et al. | |
| 2002/0081714 A1 | 6/2002 | Jain et al. | |
| 2002/0137059 A1 | 9/2002 | Wu et al. | |
| 2002/0187501 A1 | 12/2002 | Huang | |
| 2004/0077105 A1* | 4/2004 | Wu et al. | 436/524 |
| 2004/0157083 A1 | 8/2004 | Takahashi et al. | |
| 2006/0024732 A1 | 2/2006 | Huang et al. | |
| 2006/0186048 A1* | 8/2006 | Tan | 210/656 |
| 2008/0274905 A1 | 11/2008 | Greene | |

OTHER PUBLICATIONS

Roberts et al., Patterned magnetic bar array for high-throughput DNA detection, 2004, IEEE Transactions on Magnetics, vol. 40, No. 4, pp. 3006-3008.*

Groves, J.T. et al., "Micropattern Formation in Supported Lipid Membranes", Accelerated Chemistry Research, 2002, vol. 35, pp. 149-157.

Lui et al., Arrays of Magnetic Nanoparticles Patterned via "Dip-Pen" Nanolithography, Advanced Materials, vol. 14 No. 3, pp. 231-234, Feb. 3, 2002 (Abstract only).

* cited by examiner

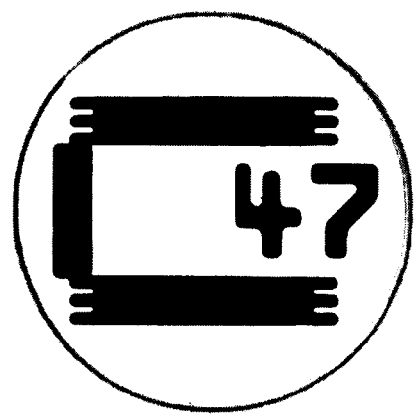
Figure 5
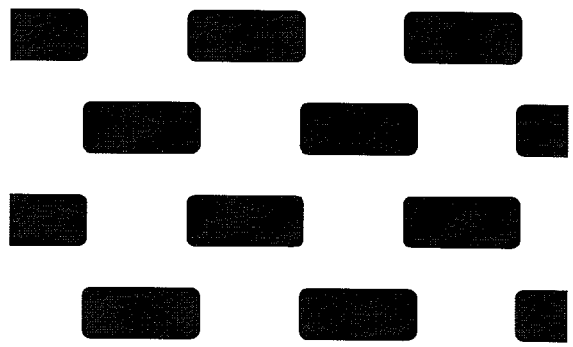
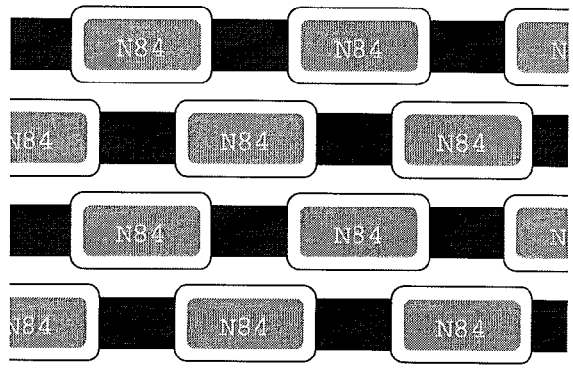
Figure 6

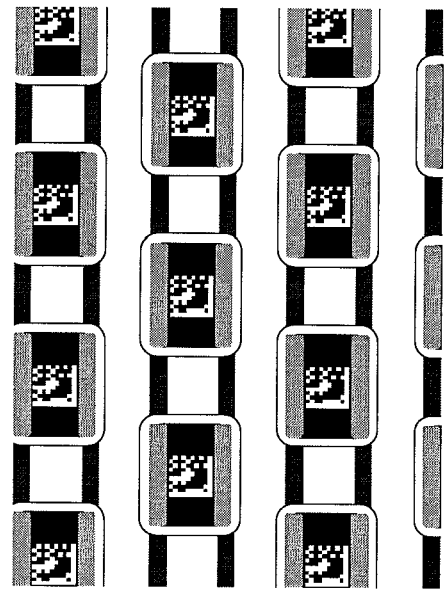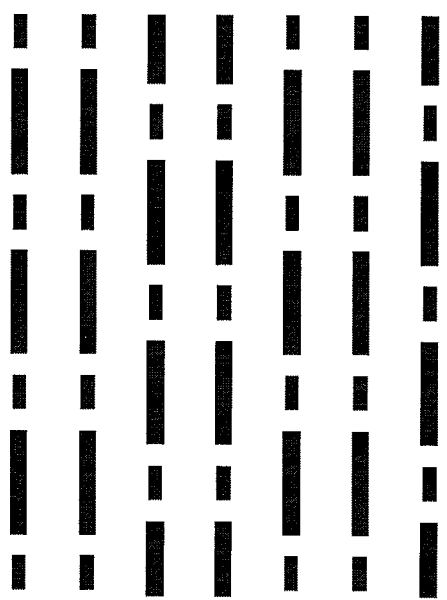
Figure 19

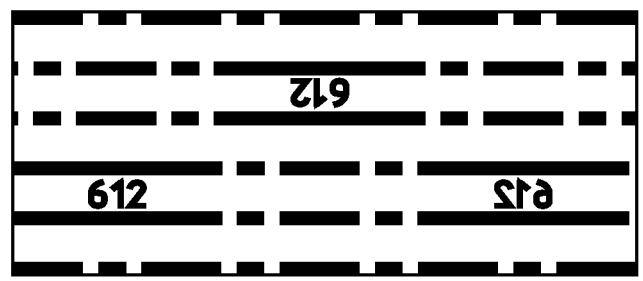
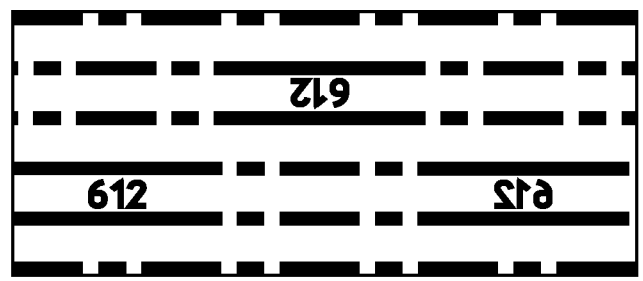
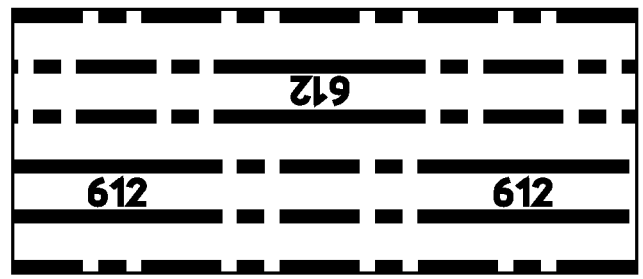
Figure 20

MICRODEVICE ARRAYS FORMED BY MAGNETIC ASSEMBLY

This application claims priority to U.S. provisional application Ser. No. 60/886,370 filed Jan. 24, 2007, and to U.S. provisional application Ser. No. 60/886,373 filed Jan. 24, 2007.

FIELD OF THE INVENTION

The present invention relates generally to the field of moiety or molecular isolation, analysis, detection, manipulation, and synthesis. In particular, the invention provides a device for manipulating and displaying microdevices by forming microparticle arrays through magnetic assembly.

BACKGROUND

Particle-based liquid array technologies offer a variety of advantages over fixed arrays, such as batch methods of moiety attachment, ease of synthesis, less cost in implementation, ease of automation, and ease of augmentation (i.e., another particle can be added to the mixture). Fixed arrays generally require less expensive reading devices than liquid arrays and they are generally more amenable to archival storage. However, the major advantage of fixed arrays, and the reason they hold a dominant position in applications requiring high multiplexing (e.g., gene expression), is that moiety identity is determined by position, thereby allowing a virtually limitless number of assays to be carried out using a fixed array platform—typical fixed arrays used in gene expression display 100s of thousands of different moieties. In contrast, liquid arrays require that each particle be encoded in order to identify the moiety each particle is displaying.

A variety of methods have been employed to solve the encoding/decoding problem of liquid arrays. One widely used approach (used by Luminex, Invitrogen via Quantum Dots, and BD Biosciences) is to incorporate fluorophors into beads. The fluorophors are mixed in differing ratios to produce the coding structure and variation. The emitted wavelengths and intensities of these fluorophor mixes are read using a technology based on Fluorescence Activated Cell Sorters (FACS). Although effective, this technology is limited by the number of dyes and intensities that can be unambiguously encoded. The limit for this method is currently between 100 to 200 codes.

BioArray Solutions has used Light-controlled Electrokinetic Assembly of Particles near Surfaces (LEAPS) to form arrays of beads on surfaces (WO 97/40385). However, the LEAPS approach is still subject to the same restrictions as bead-based techniques with respect to the types of available encoding.

A system incorporating the advantages of planar arrays and of encoded microparticles would address many of the problems inherent in the existing approaches. Illumina, Inc. has made it halfway to this goal by providing a method of generating arrays of microbeads using etched glass fibers (e.g., "High-density fiber-optic DNA random microsphere array" by Ferguson et al. Anal. Chem., 72:5618-5624 (2000)). The method involves binding a capture molecule (e.g., oligonucleotide) to a microparticle in solution and then permanently attaching the microparticle to a solid support that interfaces directly with etched glass fibers. The identity of the capture molecule on the microparticle can be identified by "visualization" of the particle through the fiber-optic cable on which it is bound. This binding, however, is not reversed and the particle remains as part of a planar array when the assay is performed—its identity being associated with its fixed location. While preparation of the array is facilitated by the liquid or 3D method, the actual assay is performed as if the array were a fixed 2D array.

Cyvera (now part of Illumina) has developed a technology that uses microparticles shaped like cans that are uniquely identified using a Bragg grating (U.S. Patent Application 2005/0220408 A1). This technique does not rely on fluorescence dye encoding and therefore has an inherently greater breadth of encoding space. Other companies have developed microparticles that do not depend on encoding using fluorophors. Nanoplex uses long and skinny photolithographically-prepared particles that are identified by differing fluorescence and reflection of bar-coded patterns composed of metals. They currently have the capacity to uniquely label 1000 of these particles and have proprietary software that identifies the location of, and decodes these particles in about one second after they have settled in a non-ordered fashion to the bottom of 96 well plate or similar. SmartBeads Technologies has microfabricated aluminum particles (e.g., strip particles having dimensions of 100×10×1 micron) encoded using multiple hole placement and decoded using an optical reading device (e.g. CCD) after being scattered on a planar surface at low density. While, in general, these and similar microfabricated particles have the advantage that they have the potential to be encoded with a nearly infinite number of patterns, the difficulty resides in the ease of analysis of mixtures of the encoded particles. Since such particles tend to be flat objects, they tend to be more prone to aggregation or overlapping as well as being more difficult to disperse.

The ability to array microparticles in an ordered fashion for analysis is advantageous. Aviva Biosciences and the research group of Eiichi Tamiya have produced and arrayed optically encoded planar particles. The Tamiya group produces and uses chemical properties to array particles (("Microfabrication of encoded microparticle array for multiplexed DNA hybridization detection" by Zhi et al. Chemical Communications, 2448-2450 (2005)). Aviva Biosciences uses the magnetic properties of their microparticles (i.e., magnetic bars encapsulated in silicon dioxide with a 2D barcode for identification) to form linear arrays or "chains" of partially overlapping microparticles in the presence of a magnetic field allowing their codes to be read (U.S. Pat. No. 7,015,047). It is also possible to form linear arrays of these magnetic particles in specially designed channels in a non-overlapping manner (U.S. Pat. No. 7,015,047). Another method of arraying Aviva's microparticles to avoid obstruction of the 2D barcode involves incorporating an excess of "accessory" or blank particles (consisting only of completely transparent $SiO_2$ with magnetic bars) into the microparticle mix. This reduces the likelihood of the encoding portion of the microparticles overlapping and increases readability (U.S. Pat. No. 7,015,047).

Although methods for arraying beads using arraying chips that consist of either arrays of magnetic bars or electromagnetic pads have been developed, these approaches suffer from similar limitations of encoding and detection as experienced by other liquid array bead-based methods.

This application references various patents, patent applications, and publications. The contents of all of these items are hereby incorporated by reference in their entirety. Where a definition or use of a term in a reference, which is incorporated by reference herein is inconsistent or contrary to the definition of that term provided herein, the definition of that term provided herein applies and the definition of that term in the reference does not apply.

SUMMARY OF THE INVENTION

The present invention provides systems and methods in which particles or other microdevices containing a predetermined preferential axis of magnetization are disposed in an array having discreet regions and oriented within a magnetic field.

Preferred microdevices are substantially rectangular, with substantially flat top and bottom surfaces. The longest linear dimension is preferably no more than 1 mm, more preferably less than 500 μM, still more preferably no more than 250 μM, and most preferably no more than 150 μM.

Preferred microdevices can have any predetermined magnetic orientation bias, which in some instances could be a bias disposed along a long axis of the microdevice, and in other instances could be a bias disposed other than along a long axis of the microdevice. The predetermined magnetic orientation bias can be implemented in any suitable manner, as for example by laying down magnetic bars during manufacture of the microdevices. Magnetic bars are preferably disposed off-center in the microdevice, but can have any suitable dimensions and orientation.

Microdevices can be coded using magnetic, photorecognizable, contact pad or other coding schemes a manner that realistically supports a coding space of at least $10^2$, $10^3$, $10^6$ or more choices for magnetic codes, up to $10^{10}$ or more choices for photorecognizable codes (for example using convention 2D bar codes such as the public DataMatrix codes), and up to $10^6$ or more choices for contact pad coding.

Microdevices can advantageously also include one or more chemically reactive sites.

Contemplated methods of forming an array of microdevices include: providing an array having discrete regions that can exert magnetic forces; providing an external magnetic field generator to direct array formation; and arraying manufactured microdevices containing a predetermined preferential axis of magnetization. In especially preferred embodiments the microdevices can be oriented in at least two, four, eight, twelve or more discrete orientations. When arrayed on the arraying device, the microdevices can completely overlap a magnetic element of the array.

In another aspect of the inventive subject matter, methods of altering orientation of microdevices include positioning the microdevices in an array and applying at least first and second magnetic fields in a sequence such that selected ones of the arrayed microdevices are re-oriented by at least 90°. Such methods are thought to be especially useful where the microdevices being arrayed have a largest linear dimension of less than 500 μM, the array is substantially disposed in plane, and the selected ones of the microdevices are re-oriented perpendicularly to the plane. Where microdevices are flipped upside down, that re-orientation can be accomplished with or without changing their locations in the array. The chemically reactive sites can be involved in combinatorial chemistry such that at least $10^2$, $10^3$, or even $10^6$ of the microdevices include mutually distinct polymers and mutually distinct magnetic, photorecognizable, electrical contact, or other codes.

Preferred arraying devices comprise an array of alternating longer and shorter magnetic bars separated by gaps, at least some of the longer bars having an average length of less than 500 μM, and at least some of the shorter bars having an average length of less than 50% of the longest bars. The longer bars can advantageously alternate in an ABABAB fashion (i.e. long-short-long-short), or in some other fashion (e.g., AABAAB, long-long-short-long-long-short). The relative size of the gaps can be significant. To aid in orienting and re-orienting the microdevices, the lengths of the shorter bars is preferably less than 60% of the gap between longer bars. In another aspect, the microdevices preferably have a length greater than the gaps such that they bridge the gaps.

Contemplated systems include those having: a magnetic field generator; an arraying chip having discrete regions that exert magnetic forces; and a set of microdevices, each of which have a predetermined preferential axis of magnetization. In preferred systems, at least some of the microdevices have a length sufficient to span a gap between first and second ones of the discreet regions. Preferred systems also utilize microdevices that have a chemically active site.

Arrays of the contemplated microdevices can combine many of the advantages of liquid arrays and fixed arrays. Individual microdevices can be reversibly arrayed on an arraying substrate by means of magnetic assembly and the orientation of the microdevice can be controlled. Preferred embodiments are also provided to produce microfabricated microdevices for magnetic assembly-based arraying.

For purposes of summarizing the claimed inventions and their advantages achieved over the prior art, certain objects and advantages of the inventive subject matter have been described herein. Of course, it is to be understood that not necessarily all such objects or advantages can be achieved in accordance with any particular embodiment. Thus, for example, those skilled in the art will recognize that the inventive concepts can be embodied or carried out in a manner that achieves or optimizes one advantage or group of advantages as taught herein without necessarily achieving other objects or advantages as can be taught or suggested herein.

All of the embodiments described herein are intended to be within the scope of the inventive subject matter. These and other embodiments will become readily apparent to those skilled in the art from the following detailed description of the preferred embodiments having reference to the attached figures, the subject matter not being limited to any particular preferred embodiment(s) disclosed.

BRIEF DESCRIPTION OF THE FIGURES

FIG. 5. Picture of round microdevice containing two three-fingered magnetic bars and an alphanumeric code with alignment bar, illuminated from below; magnification 500×.

FIG. 6. A schematic representation of a microdevice containing a single magnetic bar being arrayed. Top panel shows a portion of an arraying chip; Lower panel shows arrayed microdevices on that same portion of the arraying chip.

FIG. 19. Schematic representation of magnetic assembly of microdevices to form planar arrays where bars in the microdevices simultaneously partially and fully overlap bars on the arraying chip. Left panel shows a portion of an arraying chip and right panel shows arrayed microdevices on that same portion of the arraying chip.

FIG. 20. Actual representation of magnetic assembly of microdevices to form planar arrays shown schematically in FIG. 19, where bars in the microdevices fully overlap bars on the arraying chip. Top panel: portion of arraying chip showing an arrayed mixture of face-up and face down microdevices; Center panel: same view during application of a lifting field that lifts only the face-down microdevices; Bottom panel: same view after inverting the arraying field and turning off the lifting field—all microdevices are face-up and in the same location on the array as they were before the flipping process.

DETAILED DESCRIPTION

Figure 1:
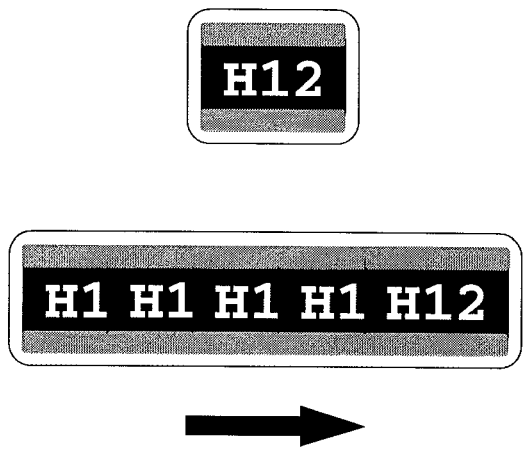
FIG. 1. Schematic of "Chain Arrays" formed by encoded microdevices containing a preferential axis of magnetization in an external magnetic field. Arrow indicates direction of the magnetic field.

Embodiments are directed to devices and methods for forming magnetically assembled arrays of microdevices and uses thereof. For clarity of disclosure, and not by way of limitation, a detailed description is divided into the subsections that follow.

DEFINITIONS

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this application is contrary to or otherwise inconsistent with a definition set forth in the patents, applications, published applications and other publications that are herein incorporated by reference, the definition set forth in this application prevails over the definition that is incorporated herein by reference. In instances where a definition is not set forth in this application and conflicting definitions arise amongst definitions incorporated herein by reference, those definitions given in U.S. Pat. No. 7,015,047 shall prevail.

As used herein, "coercivity" of a material refers to the intensity of the applied magnetic field required to reduce the magnetization of that material to zero after the magnetization of that material has been driven to saturation. Coercivity is usually measured in oersted units. A magnetic field greater than the coercivity of a material must be applied to that material in order to coerce it to change the direction of its magnetization. A "high coercivity" material is often referred to as a permanent magnet.

As used herein, a "predetermined preferential axis of magnetization" means a preferential axis of magnetization that can be predetermined through knowledge of the manufacturing process and design of the microdevice. The "predetermined preferential axis of magnetization" of a microdevice is a fundamental aspect of preferred designs. For example, bar-shaped elements of CoTaZr as used in many of the examples presented in this application have a predetermined preferential axis of magnetization that is parallel to the long axis of the magnetic bar. A "predetermined preferential axis of magnetization" is a property of a microdevice that depends on the geometry, composition, and structural configuration of the magnetic elements of the microdevice. Bar-shaped elements of CoTaZr as used in many of the examples presented in this application have a predetermined preferential axis of magnetization that is parallel to the long axis of the bar, by contrast conventional magnetic beads which have a random distribution of magnetic material do not have a predetermined preferential axis of magnetization. The induced magnetization along the predetermined preferential axis of magnetization (in its absolute magnitude) is larger than or at least equal to induced magnetization along any other axis of the microdevice. In general, for the microdevices of the present invention to rotate or orient itself under the interaction of the applied magnetic field and the induced magnetization, the induced magnetization (in its absolute magnitude) along the predetermined preferential axis of magnetization of the microdevice should be at least 20% more than the induced magnetization of the microdevice along at least one other axis. Preferably, the induced magnetization (in its absolute magnitude) along the predetermined preferential axis of magnetization of the microdevices of the present invention should be at least 50%, 70%, or 90% more than the induced magnetization of the microdevice along at least one other axis. Even more preferably, the induced magnetization (in its absolute magnitude) along the predetermined preferential axis of the magnetization of the microdevices of the present invention should be at least two, five times, ten times, twenty times, fifty times or even hundred times more than the induced magnetization of the microdevice along at least one other axis.

A. System for Forming Microdevice Arrays

In the presence of an external magnetic field a magnetic material containing a preferential axis of magnetization will align its preferential axis with said external magnetic field, unless impeded—similar to what is seen with a compass needle aligning in the magnetic field of the earth. If a collection of microdevices containing such magnets are placed together and an external magnetic field is imposed on these microdevices, and they are not impeded, they will form "chains" along their preferential axis. The length of the chains and the extent that the ends of the magnetic regions overlap depends on the strength of the external field, the physical geometry of the magnetic material, the arrangement of the magnetic material within the microdevice, and the magnetic properties of the magnetic material. FIG. 1 shows a schematic drawing of microdevices containing magnetic bars forming a "chain" when an external magnetic field is applied.

Figure 2:
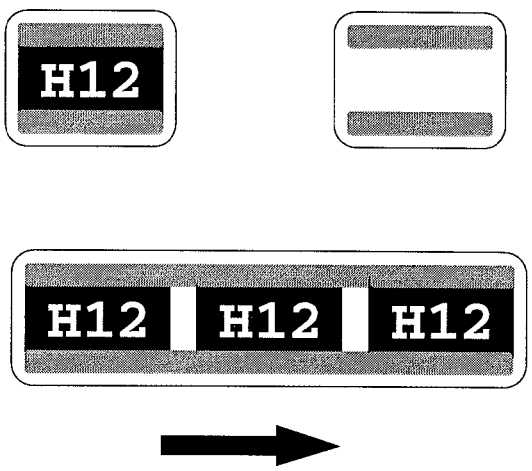
FIG. 2. Schematic representation of magnetic self assembly using "accessory microdevices" as described in U.S. Pat. No. 7,015,047.
Figure 3:
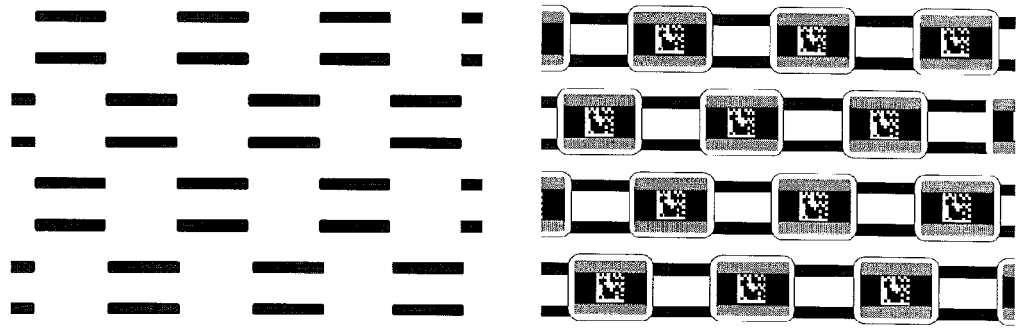
FIG. 3. Schematic representation of magnetic assembly of microdevices to form planar arrays.
Figure 4:
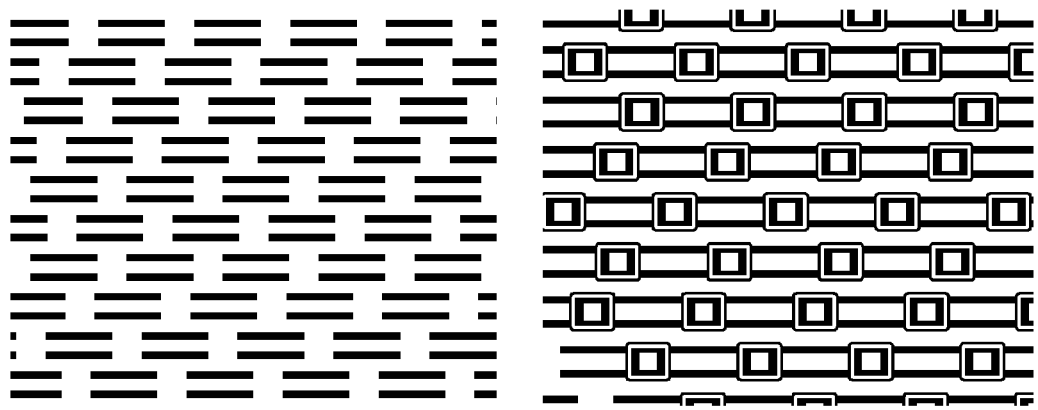
FIG. 4. Actual representation of magnetic assembly of microdevices to form planar arrays.

Microdevices containing a preferential axis of magnetization can be "arrayed" in the form of chains. If such microdevices contain optically identifiable (i.e. photorecognizable) codes, these codes can be read in their "chain arrayed" form when the extent of overlap of the microdevices in the "chain arrayed" form does not obscure the codes. FIG. 1 presents a case when the codes are partially obscured. These concepts were advanced in U.S. Pat. No. 7,015,047. Furthermore, in that patent it was suggested that transparent "accessory" microdevices that do not contain an optical code, could be mixed with optically encoded microdevices to produce "chain arrays" with a low incidence of two optically encoded microdevices being next to one another (FIG. 2). Instead of using transparent "accessory" microdevices as "spacers" during the process of self-assembly, as in U.S. Pat. No. 7,015,047, embodiments of the present invention incorporate the magnetic regions of these "accessory" microdevices into a single fixed substrate support. Thus, the resulting "chains" contain an alternating pattern of (1) a magnetic unit embedded in the substrate support, and (2) a magnetic unit within the microdevices. The substrate support, or "arraying chip", consists of an array of magnetizable material, such as the pattern of bars of the type shown in FIGS. 3 and 4. FIG. 3 shows a schematic example of this arraying process. FIG. 4 shows an actual example of the process where microdevices that are 70×90×3 microns are arrayed on a substrate containing an array of 12×152 micron bars of Cobalt-Tantalum-Zirconium (CoTaZr). The microdevices in FIG. 4 contain two 12×76 micron bars of CoTaZr.

One embodiment of the inventive subject matter includes a flat or substantially flat nonmagnetic substrate containing a pattern of "magnetic" features, as introduced previously. Features can be made out of any ferromagnetic, ferrimagnetic, or paramagnetic material. Preferred materials are high permeability ferromagnetic materials such as CoTaZr or NiFe. Preferably such features are bar shapes that have a preferential axis of magnetization. The substrate can be composed of any material that is flat or near flat. Preferred materials include Silicon, Silicon Dioxide, Silicon Nitride, glass, and plastics.

While the bar pattern of this first embodiment is similar to magnetic bar patterns used by others to capture magnetic beads (e.g., US Patent Application 2002/0081714; Yellen et al. J. Appl. Phys. 7331-7333 (2003); Roberts et al. IEEE Trans. Magn., 3006-3008 (2004)), there are several important differences between subject matter discussed herein and those earlier studies. The earlier studies rely on the field produced by the bars to trap beads, with care taken to minimize magnetic field gradients, which can cause bead clumping, while in preferred embodiments of the present invention there are considerable magnetic field gradients. More significantly, in the earlier studies, the source of the magnetic field resides on the substrate (arraying chip) surface, while here the microdevices themselves can generate fields comparable to, or greater than, the fields produced on the substrate surface. Additionally, the magnetic trapping arrays produced in earlier studies are purely attractive in nature, while the preferred staggered arrangement of magnetic bars according to aspects of the present invention also uses magnetic repulsion between the arraying chip and the microdevices to direct the arraying process.

Because at least some of the microdevices that array on the substrate, as contemplated herein, interact strongly, they spontaneously align in the presence of an external field and do not require fluid flow to become distributed over the surface of the chip as do bead-based methods. The repulsive field generated by any microdevices that are properly arrayed results in single microdevice occupation of each arraying location. These microdevices are not captured or trapped by "local fields" extending from the ends of the arraying bars, as has been described for beads (e.g., US Patent Application 2002/0081714), but are bound magnetically through physical overlap of the magnetic bars in the microdevices and the arraying chip. While earlier studies (e.g., US Patent Application 2002/0081714; Yellen et al. J. Appl. Phys. 7331-7333 (2003); Roberts et al. IEEE Trans. Magn., 3006-3008 (2004)) direct the spacing of bars to be larger than the size of the magnetic microdevice, preferred embodiments direct the spacing to be smaller, consistent with the arraying process occurring through minimization of the interaction energy by means of overlap. Taking into account the microdevice and arraying chip properties listed above, the inventive subject matter could be more aptly described as the formation of arrays by magnetic assembly rather than the formation of arrays by trapping or capture.

Fundamental differences between the current inventive subject matter and earlier published works using magnetic bars to array magnetic microdevices include:

(1) Embodiments of the current inventive subject matter use repulsive as well as attractive forces to array the microdevices.

(2) The specific controlled distribution of magnetic material within the microdevices dramatically alters the nature of the arraying process as compared to bead-based approaches where the magnetic material is randomly distributed within each bead.

(3) The ability to direct specific magnetic microdevices to different regions on the arraying chip not based on size or on the total amount of magnetic material, but on the distribution of magnetic material within the microdevice.

(4) The ability to control the orientation of the arrayed microdevice on the arraying chip.

In one aspect, the present inventive subject matter is directed to a system for forming a microdevice array, which system comprises: a) a plurality of microdevices containing one or more magnetic regions; b) a substrate containing a plurality of magnetic regions, complementary in some manner to the magnetic regions on the microdevices; and c) an external magnetic field generator.

Microdevice, Detailed Description.

The microdevice comprises a magnetizable substance wherein said microdevice has a preferential axis of magnetization. Additional features can be incorporated into the microdevice, including, but not limited to, photorecognizable coding patterns. The properties of such microdevices containing photorecognizable coding patterns are enumerated in U.S. Pat. No. 7,015,047. U.S. Pat. No. 7,015,047 discusses a subset of microdevices compatible with the magnetic assembly process.

The microdevices can have any shape. They can have planar surfaces, but they need not have planar surfaces; they can resemble beads. Flat disks are a preferred implementation. Microdevices shaped as circles, squares, ovals, rectangles, hexagons, triangles, and irregular shapes are all amenable to the magnetic assembly arraying process. Rectangular disk shaped microdevices are shown in the examples given in FIGS. 1-4. FIG. 5 shows an example of a microdevice that is a round disk. The microdevices can be of any suitable dimension(s). For example, the thickness of the microdevice can be from about 0.1 micron to about 500 microns. Preferably, the thickness of the microdevice can be from about 1 micron to about 200 microns. More preferably, the thickness of the microdevice can be from about 1 micron to about 50 microns. In a specific embodiment, the microdevice is the form of a rectangle having a surface area from about 10 squared-microns to about 1,000,000 squared-microns (e.g., 1000 micron by 1000 micron). In another specific embodiment, the microdevice is an irregular shape having a single-dimension from about 1 micron to about 500 microns.

The microdevices can contain one or many magnetizable elements. The microdevices can have a predetermined preferential axis of magnetization. A microdevice containing a single magnetic region represents the simplest example. FIG. 6 shows a schematic representation of a microdevice containing a single magnetic bar being arrayed.

Figure 7:
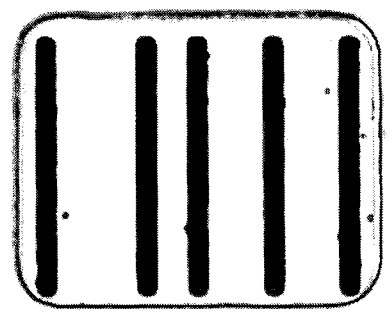
FIG. 7. A picture of microdevice with magnetic bars perpendicular to the long axis of the microdevice; illuminated from below; magnification 500×.
Figure 8:
FIG. 8. A picture of microdevice that contains rectangular magnetic bars of different lengths and an alphanumeric code; illuminated from below; magnification 500×.
Figure 9:
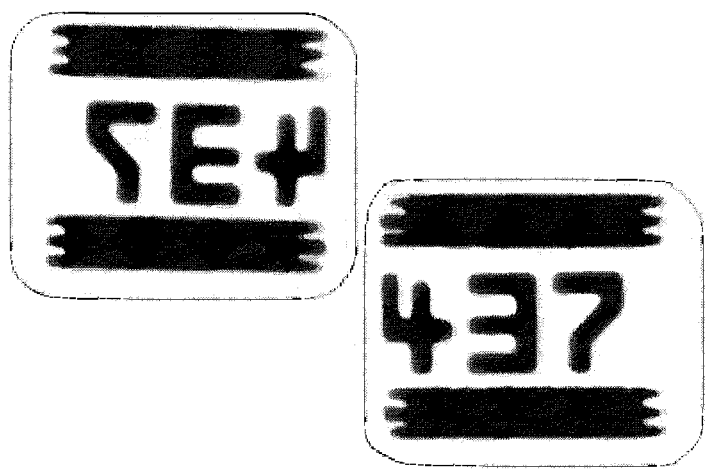
FIG. 9. Picture of rectangular microdevices containing two three-fingered magnetic bars and an alphanumeric code, illuminated from below; magnification 500×. Microdevice on lower right is "face-up". Microdevice on upper left is "face-down".

Unlike arraying of microdevices in channels (U.S. Pat. No. 7,015,047), in the magnetic assembly arraying process there is no particular advantage to the preferential axis of magnetization coinciding with the long axis of the microdevice. FIG. 7 shows a microdevice with magnetic bars perpendicular to the long axis of the microdevice. Moreover, the microdevice need not have a definable long axis (e.g., the circular microdevice shown in FIG. 5). The individual magnetic elements within the microdevice can be of any width, length, thickness and shape. FIG. 8 shows an example of microdevices containing bars of different lengths. FIG. 9 shows an example of microdevices containing three-fingered magnetic bars parallel to the long axis of the microdevice. The individual magnetic elements within a microdevice can be composed of different materials having similar or different magnetic properties.

Any suitable magnetizable material can be used in the present microdevices. In one example, the magnetizable substance used is a paramagnetic substance, a ferrimagnetic substance, a ferromagnetic substance, or a superparamagnetic substance. Preferably, the magnetizable substance is a transition metal composition or an alloy thereof such as iron, nickel, copper, cobalt, manganese, tantalum, and zirconium. In a preferred example, the magnetizable substance is a metal oxide. Further preferred materials include nickel-iron (NiFe) and cobalt. Additional preferred materials include alloys of cobalt such as CoTaZr, cobalt-iron (CoFe), cobalt-nickel-iron (CoNiFe), cobalt-niobium-zirconium (CoNbZr), cobalt niobium hafnium (CoNbHf), and cobalt tantalum hafnium (CoTaHf). Preferably such features are bar shapes that have a preferential axis of magnetization. The term "bar", in addition to rectangular shapes, includes rod-like shapes as well as slightly irregular shapes that still exhibit a preferential axis of magnetization, e.g., elongated pyramidal shapes. A bar need not be solid and can contain cutouts or holes as described below. The magnetizable substance can be situated completely inside (encapsulated) the non-magnetizable substrate comprising the microdevice, completely outside yet attached to the non-magnetizable substrate comprising the microdevice, or anywhere in between. Preferably the magnetizable substance is patterned, for example using micromachining or lithographic techniques, so that its three-dimensional shape is a known feature of the design of the microdevice.

Because the microdevices are used to carry out assays in a liquid array format, it is advantageous that they can be conveniently aliquoted or dispensed using conventional liquid and bead handling devices (e.g. pipettors). Consequently, it is desirable that they do not self-associate in the absence of a magnetic field. Therefore, low remanence (i.e., magnetization left behind in a medium after an external magnetic field is removed) is a desirable quality. Cobalt alloys such as CoTaZr and iron oxides ($Fe_3O_4$) are preferred examples of magnetic materials that meet this criterion.

In a preferred embodiment, microdevices include a non-magnetic substrate composed of multiple layers, as described in U.S. Pat. No. 7,015,047. This non-magnetic substrate can contain other features including optical encoding patterns (as shown in FIGS. 5, 7, and 8) and wells. Additional features can be included and any of the wide range of features compatible with planar microfabricated devices such as those used in Micro-Electro-Mechanical Systems (MEMS) can be incorporated into the non-magnetizable substrate of the microdevice. In a preferred embodiment the microdevice contains electrical contact pads and circuitry that allow MEMS type sensors within the microdevice to be utilized. This circuitry is composed of electrically conductive material that is preferably encapsulated within the substrate of the microdevice such that only contact pads and sensor elements are exposed on the surface of the microdevice. Contact pads on the surface of the microdevice can be used to connect the microdevice to a power source(s) and/or sensing device(s) by means of complementary contact pads on the arraying chip. In a preferred embodiment, electrical circuitry is placed within each microdevice in a unique configuration, thus the connection between the microdevice contact pads and the complementary pads on the arraying chip may be used to determine the identity of the microdevice.

In one embodiment the microdevices comprise a chemically reactive surface that is suitable for attachment of a chemical or biological moiety. In another embodiment this surface is present in a well or indentation. In one embodiment this surface is produced by means of a silane (e.g. aminopropyltrimethoxysilane, gycidoxypropyltrimethoxy silane). In another embodiment a reactive surface is produced by means of a thiol containing reagent (e.g. 11-mercaptoundecanoic acid). In another embodiment the reactive surface is a self-assembled monolayer (for example as reviewed in "Formation and structure of self-assembled monolayers" by Ulman Chem. Rev. 96:1533-1554 (1996) and "Self-assembled monolayers of thiolates on metals as a form of nanotechnology" by Love et al. Chem. Rev. 105:1103-1169 (2005)). The reactive surface can be generated on the microdevice using batch techniques (e.g. a set of microdevices placed in an aqueous solution of the appropriate reagent, such as silane to generate a reactive surface on exposed silicon dioxide surface of the microdevice). Alternatively, the reactive surface can be generated on the microdevices prior to their release from the wafer (during or after the fabrication process). The reactive surface can be applied to all the microdevices on the wafer (e.g. by gas or liquid phase silanization) or at particular positions on the wafer using position specific deposition (e.g. inkjet) or masking (e.g. photolithography) such that the reactive surface is applied only to a subset of microdevices on the wafer or even to specific locations on individual microdevices. In a further embodiment such position specific processes can be used to produce unique chemical compounds on individual microdevices. Such techniques are widely used to produce DNA microarrays and are well-established art (e.g. "Spatially addressable combinatorial libraries" by Pirrung Chem. Rev. 97, 473-488 (1997) and "In situ synthesis of oligonucleotide microarrays" by Gao et al. Biopolymers, 73:579-596 (2004)). In a further embodiment the locations of reactive surface on individual microdevices can be patterned. Such patterning can be generated by masking in which a material is used to protect a surface from being modified, for example a layer of photoresist can be used to surround a silicon dioxide well and then following the silanization of the well surface the photoresist can be dissolved away to reveal a unsilanized surface. Patterning can also be achieved through the use of different materials, for example a gold surface can be created on a silicon dioxide surface, reaction with a carboxylated alkyl thiol will yield a carboxylated surface only over the gold. Individual microdevice can contain one or many patterned reactive surfaces. Such methods are well established in the fabrication and chemical literature particularly as applied to the manufacture of DNA and protein microarrays. In additional embodiments the chemically reactive surface corresponds to a linker molecule used in solid phase synthesis. Many such linker molecules are known to those practiced in the art of combinatorial chemistry (e.g. as referenced in Jung, G., *Combinatorial Chemistry*, Weinheim, Wiley-VCH, 1999; "Comprehensive survey of chemical libraries for drug discovery and chemical biology; 2006" by Dolle et al. Journal of Combinatorial Chemistry, 9:855-902 (2007)).

When a microdevice that contains magnetic elements is placed in an external magnetic field, a magnetic dipole(s) is induced in the microdevice. Because the microdevice has a preferential axis of magnetization it will, unless impeded, rotate so as to align its preferential axis of magnetization with the force lines of the external magnetic field. When placed in a rotating external magnetic field the microdevices, unlike conventional magnetic beads, will rotate and, in effect, serve as mini stir-bars. Consequently it is desirable, apart from any considerations with respect to arraying, that the microdevices respond strongly to external magnetic fields. Magnetic elements composed of materials with high saturation magnetizations such as CoTaZr alloys are a preferred embodiment.

Arraying Chip, Detailed Description.

The arraying chip is comprised of both magnetic and non-magnetic material. Any suitable magnetizable material can be used in the arraying chip. In one example, the magnetizable substance used is a paramagnetic substance, a ferromagnetic substance, a ferrimagnetic substance, or a superparamagnetic substance. Preferably, the magnetizable substance is a transition metal composition or an alloy thereof such as iron, nickel, copper, cobalt, manganese, tantalum, and zirconium. In a preferred example, the magnetic substance is a metal oxide. Further preferred materials include NiFe and cobalt. Additional preferred materials include alloys of cobalt such as CoTaZr, CoFe, CoNiFe, CoNbZr, CoNbHf, and CoTaHf. Preferably such features are bar shapes that have a preferential axis of magnetization. In many applications residual magnetization in the arraying chip is a desirable quality. Similar to the microdevice, the magnetizable substance in the arraying chip can be situated completely inside (encapsulated) the non-magnetizable substrate comprising the arraying chip, completely outside yet attached to the non-magnetizable substrate comprising the arraying chip, or anywhere in between. A preferred embodiment places the magnetic elements on top of a glass substrate and encapsulates them with silicon dioxide such that the silicon dioxide forms a planar or substantially planar surface.

Although the examples presented in this application use an arraying chip containing CoTaZr bars that have low remanence and low coercivity, these properties are not necessary for the assembly of magnetic arrays. Since high remanence will cause microdevices to magnetically assemble into chains or clumps in the absence of an external magnetic field, in general, it is not desirable for the microdevices to contain such; although, it can be desirable that the magnetic elements contained within the arraying devices have said qualities in order to allow assembled arrays to remain intact once the arraying field is removed. However, arrays can also be analyzed dry and the adhesive forces between the flat microdevices and the surface of the arraying chip will be sufficient to hold the arrayed microdevices in place under most experimental conditions in the absence of a continuously applied external magnetic field. These adhesive forces can be enhanced by drying under condition or in the presence of reagents where drying leaves a film over the surface.

The individual magnet elements within the arraying chip can be composed of different designs. The magnetic elements can be of any shape and size. Individual magnetic elements can be distinct from all other elements or comprise a subset of such elements. The individual magnetic elements can be composed of different materials having similar or different magnetic properties. Preferably the magnetic elements are bar shapes that have a preferential axis of magnetization. More preferably the magnetic elements have a predetermined preferential axis of magnetization. The term "bar", in addition to rectangular shapes, includes rod-like shapes as well as slightly irregular shapes that still exhibit a preferential axis of magnetization, e.g., elongated pyramidal shapes. A bar need not be solid and can contain cutouts or holes as described below.

A preferred embodiment is magnetic elements that are bars composed of a high permeability ferromagnetic material. These bars can be rectangular or substantially rectangular as shown in the examples in FIGS. 5 and 8. Bars containing "fingers" such as those shown in FIG. 5 and described in U.S. Pat. No. 7,015,047 are another preferred embodiment. These fingers can be short (e.g., 1-2% of the total length of the bar) or long (e.g., comprising almost the entire length of the bar) or anywhere in between.

The non-magnetizable substrate can be comprised of any suitable material including silicon, silicon dioxide, silicon nitride, plastic, glass, ceramic, polymer, metal (e.g., gold, aluminum, titanium, etc.) or other similar materials or combinations of such materials. In a preferred example the material is silicon dioxide. In another preferred example the material is glass. The substrate can comprise a single layer or it can comprise multiple layers. The arraying chip substrate can, but need not be, planar or substantially planar. There can exist indentations in the arraying chip that allow for "seating" of the microdevices to assure exact alignment of said microdevices, which can be desirable for some applications. These indentations, for example, can have planar faces for seating of microdevices that are flat-ish, or they can be spherical for seating of beads or bead-like microdevices. In one preferred embodiment the indentations are designed to match the shape of individual planar microdevices, e.g. rectangular wells to hold rectangular microdevices of the type shown in FIGS. 7, 8, and 9.

The number of arraying sites per unit area is dependent on the size and spacing of the magnetic elements on the arraying chip. For example, arraying chips of the type shown in FIG. 4 that are arraying microdevices that are 70×90 micron in size can array approximately 70 microdevices per square millimeter. In other embodiments the density will be much higher. For example, microdevices of the type shown schematically in FIG. 6, that are 5×10 micron in size can be arrayed at a density of approximately 10,000 microdevices per square millimeter.

The arraying chip can contain additional features that are not necessarily required to facilitate the arraying process. Any of the wide range of features compatible with planar microfabricated devices can be incorporated into the non-magnetizable substrate of the arraying chip, such as those used in MEMS (for example as reviewed in Liu, C., *Foundations of MEMS*, Pearson Prentice Hall, Upper Saddle River, N.J., 2006; Gad-el-Hak, M., *MEMS (Mechanical Engineering)*, CRC Press, Boca Raton, 2006). A preferred example is microchannels. Such channels can be used to deliver and/or remove reagents and other materials such as microdevices from the arraying chip surface. Additional preferred examples include electronic and optical microsensors including those used in MEMS (for example as reviewed in Gardner, J. W. et al., *Microsensors, MEMS, and Smart Devices*, John Wiley & Sons, West Sussex, 2001).

In a preferred embodiment an arraying chip contains electrical contacts and circuitry. This circuitry allows electrical impulses to be sent through the arraying chip to specific locations on the array. This circuitry is composed of electrically conductive material that is preferably encapsulated within the substrate of the arraying chip such that only contact pads are exposed on the surface of the arraying chip. Contact pads on the outer edge or surface of the arraying chip can be used to connect the arraying chip to power sources and/or sensing devices. Contact pads within the array can be used to make electrical contact to arrayed microdevices on the arraying chip surface. Such circuitry and electrical contacts can be used to power and/or receive signal from MEMS type sensors in the microdevice. In a preferred embodiment these electrical pads are used for identification of the microdevice. When the microdevice containing electrical contact pads is arrayed on an arraying chip containing a complementary contact pad an electrical signal can be sent through the arraying chip and through the arrayed microdevice. In a preferred example the pattern of contact pads on the arraying chip is non-variable (it is the same at each location on the array) while the pattern microdevices is varied such that measuring an electrical property such as resistance or conductivity of an arraying chip site will allow the identity of the arrayed microdevice to be determined.

In a preferred embodiment the arraying chip contains a series of separate arrays. Such arrays can be separated by channels or walls on the surface of the nonmagnetizable substrate or can only be divided by empty space. In the case of walls, the walls can be made of any material compatible with the substrate surface including silicon dioxide, silicon nitride, plastic, glass, ceramic, polymer, metal (e.g., gold, aluminum, titanium, etc) or other similar materials or combinations of such materials. A preferred embodiment is SU-8.

In another preferred embodiment a template is placed over the arraying chip to physically separate the individual arrays into compartments. Such templates can be made out of a wide variety of materials including plastics and metals. PDMS is a preferred material.

In another preferred embodiment the arraying chip contains labels, codes, or alignment marks to assist in the reading and analysis of arrayed microdevices.

Figure 10:
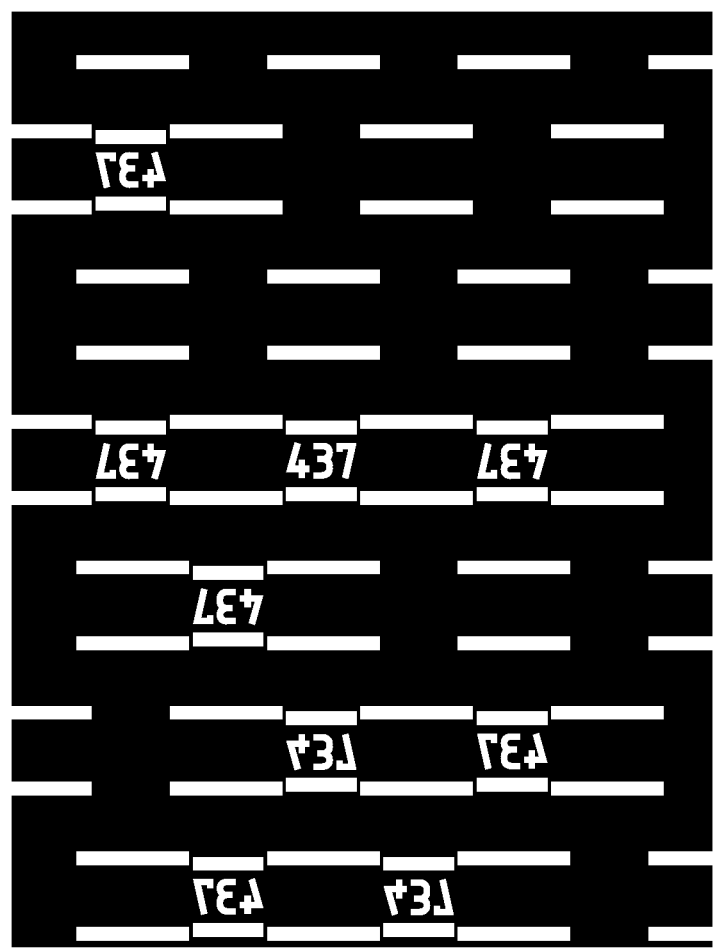
FIG. 10. Actual representation of magnetic assembly of microdevices to form planar arrays as described herein but without perfect matching between magnetic elements. Microdevices contain magnetic bars of 10 micron width and 30 micron spacing while magnetic bars in arraying chip are 12 micron in width and spaced 32 micron apart FIG. 11. Microdevices on an arraying chip in the presence of an arraying field (x-axis) and a lifting field (z-axis). Left panel: no lifting field; Center panel: same view with positive lifting field; Right Panel: same view with negative lifting field.

The magnetic elements of the arraying chip should be complementary to those of the microdevice, but need not exactly match those of the microdevice in dimension or shape. For example, as shown in FIG. 10, microdevices containing magnetic bars of 10 micron width and 30 micron spacing successfully magnetically assemble with magnetic bars that are 12 micron in width and spaced 32 micron apart.

Fabrication.

Microdevices and arraying chips may be fabricated using any of a variety of processes. In preferred embodiments they are produced using variations of conventional micromachining and semiconductor fabrication methods. Such methods are described and referenced in U.S. Pat. No. 7,015,047 and US Patent Application 2002/0081714 as well as in reviews and textbooks that discuss photolithographic or MEMS fabrication techniques (for example in Banks, D., Microengineering, MEMS, and Interfacing: A Practical Guide, CRC Press, 2006).

Magnetic Field Generators, Detailed Description.

The magnetic fields necessary to drive the magnetic assembly arraying process can be produced by electromagnets, permanent magnets, or a combination of the two. In the examples presented below all three approaches have been used to successfully generate an assembled array of microdevices. The strength of the external magnetic fields that are compatible with the magnetic assembly process is very broad and external magnetic fields as small as 2 Oe and as large as 300 Oe have been used successfully. Field strengths outside of this range should also be acceptable.

In a preferred embodiment the magnetic field generator consists of a set of nested electromagnetic coils (e.g. Helmholtz coils) that direct magnetic fields along multiple axes (e.g. x,y,z). In another preferred embodiment, the magnetic field generators consist of individual nested sets of electromagnetic coils, similar to Helmholtz coils but wherein the individual coils that would comprise a Helmholtz coil can be independently regulated. In a further preferred embodiment the coils contain magnetic cores such as iron or ferrite. In another preferred embodiment the magnetic field generating system contains a DC power supply capable of producing outputs of either positive or negative polarity. In another preferred embodiment the magnetic field generating system contains an AC power supply or a frequency generator coupled with an amplifier capable of driving the electromagnetic coil. In a further preferred embodiment the magnetic field generating system contains an AC power supply suitable for generating a demagnetizing pulse.

Magnetic Array.

On the arraying chip the magnetic elements are fixed. In the "accessory" microdevice system (FIG. 3) magnetic self-assembly occurs in the presence of external magnetic fields in any direction as long as the magnetic force is sufficient to overcome non-magnetic forces that can impede assembly of the microdevices, including, adhesive forces between microdevices, viscous drag, and gravitational forces.

In preferred embodiments of the present inventive subject matter, where magnetic assembly occurs between the arraying chip and the microdevices, in addition to overcoming non-magnetic forces that can impede assembly, there is also a magnetic competition in which the microdevices are attracted both to each other (self-assembly) as well as to the magnetized elements on the arraying chip (arraying). The microdevices will orient in the direction of the external field, while the orientation of the magnet elements on the arraying chip remains fixed. Under optimal arraying conditions the external field is aligned parallel to, or substantially parallel to, the principle axis of the magnetic elements of the arraying chip. Under these conditions the magnetic dipoles of the magnetic elements in the arraying chip and the microdevices are aligned, thus maximizing the strength of energetically favorable magnetic assembly as well maximizing the strength of repulsive interactions between self-associated microdevices and the arraying surface.

For arraying chips containing magnetizable elements (e.g., magnetizable bars), the relative strength of the fields generated by the magnetic elements within the microdevices, and those on the arraying chip, is dependent on the amount of material used to form the magnetic elements, the geometry of the magnetic elements, and the magnetic properties of the magnetic material used. In the examples shown in FIGS. 5, 7, 8 and 9, all bars have been made from the same material—CoTaZr. This particular alloy, in a ratio of 92:4:4, has a high saturation magnetization, little remanence and zero magnetostriction. The magnetic elements on the arraying chips that were used are twice as thick or deep as the magnetic elements in the microdevices (i.e., 0.8 micron versus 0.4 micron) and range in length from equivalent to 2.5-times longer, and in width from equivalent to 1.2-times wider. In general, the expected fields generated near the end of the magnetic regions in the arraying chips were 2- to 4-times greater than the fields generated by the magnetic regions in the microdevices. As discussed below, the arraying process should work well even if these ratios are reversed.

B. Methods of Forming a Microdevice Array

In another aspect, the present inventive subject matter is directed to a method of forming a microdevice array, which method comprises: a) providing a plurality of microdevices, each of the microdevices comprising magnetizable elements, wherein said microdevices have a predetermined preferential axis of magnetization; b) providing an arraying chip, said arraying chip containing a plurality of fixed magnetic elements complementary to those of the microdevice; c) one or more external magnetic field generators; d) introducing said plurality of microdevices onto said arraying chip; and e) manipulating said microdevices upon said arraying chip by magnetic and/or other forces, whereby the combined effect of said forces, the distribution of magnetic elements of said arraying chip, and the distribution of magnetic elements of said microdevices substantially displays the microdevices in an ordered pattern on the surface of the arraying chip.

The basic arraying process involves the assembly of two sets of complementary magnetic elements, those in the microdevices and those in the arraying chip. One or more magnetic field generators can be used to direct the arraying process. For simplicity it is easiest to consider three separate magnetic fields, each directed along the x, y or z axis of a Cartesian-coordinate system. Uniform, essentially unidirectional, fields can be generated by Helmholtz coils. A set of three nested Helmholtz coils can be used to generate the magnetic forces required in this exemplary discussion of magnetic arraying. The strength of the individual magnetic fields can be rapidly altered by varying the current sent through each. By using relays or bipolar power supplies (power supplies that allow a negative voltage) the direction of the magnetic field can be inverted.

The first external magnetic field (the "arraying field") is directed along the axis of the magnetic bars in the arraying chip to drive the arraying process. For clarity, the arraying axis will be defined to coincide with the x-axis. A second external magnetic field (the "lifting field") is directed perpendicular to the plane of the arraying chip (along the z-axis). A third external magnetic field (the "rotation field") in the plane of the arraying chip is directed perpendicular to the axis of the arraying bars (along the y-axis). The arraying field is used to drive magnetic assembly between the microdevices and the arraying chip to produce properly arrayed microdevices as shown in FIGS. 4 and 10. The lifting field and the rotation field are used to dislodge improperly arrayed microdevices and move them around the arraying chip until they are properly arrayed.

Magnetic Assembly.

Others have demonstrated magnetic arraying of beads using "localized magnetic fields", where the beads are captured between adjacent magnetic bars that comprise a fixed array similar to that shown in FIG. 4 (US Patent Application 2002/0081714; "Printing superparamagnetic colloidal microdevice arrays on patterned magnetic film" Yellen et al. J. Appl. Phys. 7331-7333 (2003); "Patterned magnetic bar array for high-throughput DNA detection" by Roberts et al. IEEE Trans. Magn., 3006-3008 (2004)). "Localized magnetic field" as defined by US Patent Application 2002/0081714 is "a magnetic field that substantially exists in the volume between the north pole of a first magnetic region and the south pole of a second magnetic region."

In other aspect, the dominant magnetic interactions need be in the space between magnetic elements, but rather within those elements. Moreover, unlike magnetic capture, as described above, where magnetic attractive forces dominate, in the magnetic assembly processes presented herein repulsive magnetic contributions are vital to the process. Consequently, microdevices on the surface of an arraying chip in an external magnetic field can be efficiently arrayed even if the attractive force between microdevices is greater than the attractive force between the microdevices and the arraying surface. This is because self-association of microdevices would require unfavorable repulsive interactions between the magnetic regions of the arraying chip and the self-associating microdevices. For example, consider the arrays shown in FIGS. 4 and 10, with a homogeneous magnetic field along the x-axis (the long axis of the magnetic bars in FIGS. 4 and 10). The relevant free energy relationship required for arraying versus self-assembly is that the energy for arraying, $E_{AR}$, be less than the energy of self assembly, $E_{SA}$, plus the energy of repulsive interactions, $E_{RI}$, between the arraying chip and the microdevices. The strength of each of these interactions will be proportional to the product of the magnetic pole strengths; $m_{MD}$ for the microdevices and $m_{AC}$ for the arraying chip. The relevant relationships are as follows:

$$E_{AR} \propto m_{MD} \cdot m_{AC}; \ E_{SA} \propto m_{MD} \cdot m_{MD}; \ E_{RI} \propto m_{MD} \cdot m_{AC} \quad (1)$$

where $E_{RI}$ is opposite in sign from the other two energy terms. Based upon these relationships self-assembly among microdevices is favored when $m_{MD} \gg m_{AC}$ and arraying is favored when $m_{AC} \gg m_{MD}$. When $m_{MD}$ and $m_{AC}$ are of similar magnitude the sum of the energies of self-assembly, $E_{SA}$, and of the repulsive interactions, $E_{RI}$, effectively cancel and arraying is strongly favored. Moreover, the strength of the interactions that direct arraying (i.e., $E_{AR}$ and $E_{RI}$) are at a maximum when $m_{AC} = m_{MD}$. Consequently, if the strength of the magnetic elements on the arraying chip and within the microdevices differed to a great extent (i.e., orders of magnitude) then the magnetic assembly process would be less effective. In the case where the magnetic elements within microdevices are overly dominant the primary interaction would be self-association of microdevices. In the case where the magnetic regions of the arraying chip are overly dominant, stacking of microdevices can be observed; repulsive interactions similar in magnitude but opposite in sign from $E_{SA}$ prevent multiple microdevices from occupying the same arraying position on the arraying chip. This additional repulsive process is another fundamental difference between bead-based arraying and the magnetic assembly arraying described herein.

Arraying by Magnetic Assembly.

In the magnetic assembly arraying processes presented herein, the magnetic features have a preferential axis of magnetization. In the presence of an applied external field, H, the field inside the magnetic feature H', is different than the applied field due to a demagnetization factor. For ferromagnetic and ferrimagnetic materials H' is less than H. The shape and composition of the magnetic feature determines its demagnification factor and the distribution of "magnetic charge" on the surface of the magnetic feature.

There are various computer programs such as FEMM (http://femm.foster-miller.net), MagNet (http://www.infolytica.com), FEMLAB (http://www.femlab.com) ("Magnetism and microfluidics" by Pamme Lab Chip, 6:24-38 (2006)) that can be used to model the magnetic assembly arraying process and its multiple magnetic elements. Someone of ordinary skill in the art will be able to use such programs to model the magnetic properties of the microdevices and the arraying chip. However, a few simple assumptions allow qualitative and semi-quantitative conclusions to be drawn about the process of arraying by means of magnetic assembly.

For example, consider the case of arrayed magnetizable bars of the type shown in FIGS. 3, 4, 6, and 10. The interaction distance between the ends of the separate bars is significantly less than the length of the bars and the distance between opposite poles within any individual bar. Consequently, the force between each overlapping bar in the arrayed state in the presence of a uniform external magnetic field in the direction of the long axis of the bars can be approximated as the interaction between isolated magnetic poles (i.e., Coulomb's Law) ("Two magnets and a ball bearing: A simple demonstration of the method of images" by Poon Am. J. Phys., 71:943-947 (2003)), such that $$F \propto \frac{m_1 m_2}{r^2} \quad (2)$$

where F is the force between the two magnetic poles, r is the distance between them, and $m_1$ and $m_2$ are the respective pole strengths.

In the arraying process shown in FIGS. 3, 4 and 10 there are four such interactions when the microdevices shown in those figures are in their properly arrayed form.

Consider an isolated unimpeded microdevice suspended in a fluid under idealized conditions (e.g., fluid of equal density, negligible surface tension, and absence of adhesive forces) at the center of three nested orthogonal Helmholtz coils (able to generate unidirectional uniform magnetic fields). A uniform external magnetic field is applied along the x-axis. Since the field is uniform there is no translational force on the microdevice, there is however a torque, τ.

$$\tau = \mu B \sin \theta \quad (3)$$

where μ is the magnitude of the magnetic dipole, B is the magnetic field, and θ is the angle between the magnetic field and the magnetic dipole. The microdevice will rotate to align its magnetic elements with the external field, e.g. the bars will align with the x-axis (torque goes to zero).

When a second uniform external field along the y-axis is applied the isolated microdevice will experience additional torque, as described by equation 3. The microdevice will rotate so as to reduce the torque to zero. Consequently, if the fields in the x and y directions are equal in magnitude the microdevice will orient with an angle of 45 degrees to the x- and y-axes. If the fields are applied simultaneously the rotation to the equilibrium position will be random. If the fields are applied sequentially, upon application of the second field all of the microdevices will rotate in the same direction to the new equilibrium position since the first field has established a polarity in the magnetic elements. Similarly, if an additional uniform external field is applied along the z-axis the microdevice will again attain an equilibrium position so as to eliminate the torque on the microdevice.

Now consider the same process except with the addition of an arraying chip of the type shown in FIGS. 3, 4, and 10 with its bars aligned with the x-axis. When the field is applied along the x-axis the microdevice will interact with the magnetic elements of the arraying chip and achieve an arrayed conformation. Application of a second field along the y-axis will apply a torque to the arrayed microdevice. However, even if the field along the y-axis is equal in magnitude to the field along the x-axis the microdevice will not rotate. This is a consequence of the arraying force holding the microdevice in place. The rotation becomes quantized (i.e., until the torque exerted by the field along the y-axis is greater than the arraying force the microdevice remains arrayed). Once the torque exceeds that threshold the microdevice rotates to align substantially along the y-axis. This is not a thermodynamically reversible process even in an idealized model. The arraying force as shown in eqn 2 is dependent upon the distance between the magnetic poles in the arrayed state. Once the microdevice has rotated out of the arrayed state the distance between the magnetic charges has become large. Consequently, after applying a field in the y-direction sufficient to disarray the microdevice, a small decrease in the magnitude of that field will not cause the microdevice to array.

Figure 11:
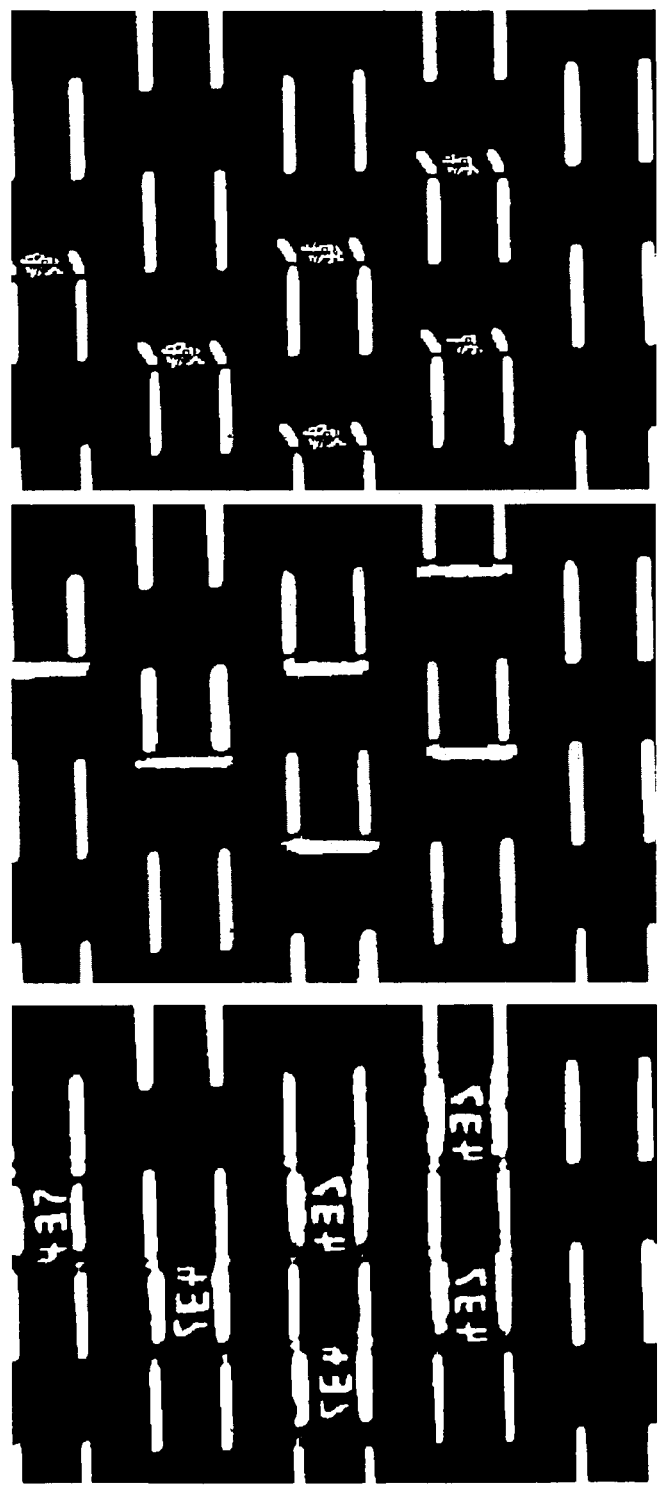

Similarly, a second external field applied along the z-axis will result in quantized movement, but the process is significantly more complicated. Rotation of the microdevice to align with the z-axis does not result in the microdevice losing all favorable contacts with the arraying chip surface. Fully upright microdevices (i.e., aligned substantially with the z-axis) will maintain a strong magnetic interaction with the magnetic elements of the arraying chip, as shown in FIG. 11.

In practice, there will be many microdevices placed on the arraying chip surface. A uniform field directed along the x-axis will not array every microdevice since not all microdevices will land on or near empty arraying positions. The purpose of the non-arraying fields, those in the y- and z-directions, is to move the microdevices over the surface of the arraying chip and facilitate efficient arraying. The arraying field can also be used to move non-arrayed microdevices and facilitate arraying since field gradients can be introduced into the arraying field without adversely affecting the arraying process, e.g. by rapidly cycling the direction of the arraying field multiple times per second. Other forces, either alone or in conjunction with magnetic fields, can also be used to redirect misarrayed microdevices. Such forces include vibratory forces as well as fluidic force, acoustic force, diaelectrophoretic force, etc. as described in US Patent Application 20020137059. This process can also be used to remove defective or damaged microdevices as well as direct orientation, as discussed below. In one example, the additional force is created by movement of the arraying chip in the presence of the magnetic field generator. This movement can involve movement in any direction and in a preferred embodiment it involves rotation of the arraying chip.

Another aspect, not covered in the simple example using a single microdevice, is magnetic self-assembly of multiple microdevices. As discussed above, in the presence of only an arraying field the microdevices do not self-assemble (because of repulsions between magnetically associated microdevices and the arraying chip's magnetic elements). When a field is added along the z-axis very little self-association occurs. This is because the microdevices are on the surface of the arraying chip and can be drawn to open positions on the arraying chip by the magnetic elements on the arraying chip. Because the microdevices that align with the field along the z-axis are upright they have little direct surface contact with the arraying chip surface. Consequently, the microdevices tend to readily distribute across the arraying chip surface and find a vacant pair of magnetic dipoles on the arraying chip with which to directly interact. While some upright chains of self-assembled microdevices can form early in the arraying process in the presence of a strong magnetic field directed along the z-axis, after a few cycles varying the lifting field (i.e., z-axis) essentially all of the microdevices can be magnetically bound to the surface. By contrast when a strong magnetic field is applied along the y-axis significant self-assembly can occur since unfavorable magnetic repulsions between the self-associated microdevices and the arraying chip are minimized.

In practice, z-axis disarraying can be easily reversed since the orientation along the x-axis is maintained and as the magnetization along the z-axis is decreased gravity and buoyant forces assist in directing the microdevice toward the arraying chip surface. Consequently, application of a rotating magnetic field in the x-z plane, sufficient to lift misarrayed microdevices when optimally aligned with the z-axis, can lead to efficient arraying. Properly arrayed microdevices, when disarrayed by a magnetic field along the z-axis, can have the same orientation along the x-axis when in their upright position, either on the left or on the right side of the gap between the bars, the position controllable by changing the direction of either the x- or z-fields (as shown in FIG. 11). For rotations along the y-axis there are potential adhesive interactions between the microdevice and the arraying chip surface.

The quantized disarraying effect can be used to drive the arraying process. Once microdevices are arrayed, applying fields along the y- and z-axes that are just under the threshold of what is required to disarray properly arrayed microdevices can cause improperly arrayed or damaged microdevices to be moved over the surface of the arraying chip. Even in uniform external fields microdevices can move over the surface of the arraying chip attracted by magnetic fields generated by magnetic elements in the arraying chip that are not occupied by a microdevice.

A non-uniform field in the x-y plane can be utilized to spread the microdevices over the surface of the arraying chip more efficiently. In a preferred embodiment an alternating field gradient is applied in the x and y directions. Such fields can be generated using Helmholtz type coils or similar coils including those containing magnetic cores and rapidly reversing the direction of the magnetic field. Such fields can also be generated by using individual electromagnetic coils (e.g., a Helmholtz-type design where the coils can be energized separately or an electromagnetic stirrer such as those sold commercially by Variomag), or by use of movable permanent magnets (e.g. a motor driven magnetic stirrer such as those sold commercially for use in chemical laboratories), or a combination of permanent and electromagnetic coils.

One parameter that is an important variable in this arraying process is the thickness of the non-magnetic layers covering the magnetic elements in both the arraying chip and the microdevice. As shown in eqn 2 the strength of the arraying interaction is dependent on the inverse square of the distance. In the magnetically assembled state this distance is equal to the sum of the thicknesses of the encapsulating nonmagnetic materials that cover the magnetic elements, i.e.

$$F_{Arraying} \propto \frac{1}{(d_{MD} + d_{AC})^2} \quad (4)$$

where $d_{MD}$ represents the thickness of the encapsulating layer on the microdevice and $d_{AC}$ represents the thickness on the encapsulating layer on the arraying chip. These thicknesses affect the strength of microdevice self-association as well as the strength of the arraying force between the arraying chip and the microdevices, i.e. the force for self-association $F_{SA}$ can be written as:

$$F_{SA} \propto \frac{1}{(d_{MD} + d_{MD})^2} \quad (5)$$

As discussed earlier, optimal arraying occurs when arraying dominates over self-association. From eqns 4 and 5 this occurs when $d_{MD} \gg d_{AC}$. However, no matter how much larger $d_{MD}$ is than $d_{AC}$ the ratio of the forces will not exceed a factor of approximately four. Since increasing distance between magnetic poles results in weaker interactions between the arraying chip and the microdevice, large absolute values of $d_{MD}$ are not desirable. The appropriate choice for these distances depends on the particular application, the size of the magnetic elements, the magnetic properties of the materials, and the size and density of the microdevices. For microdevices of the type and size shown in FIGS. 7, 8, and 9 a value of $d_{MD}$ of approximately 1 to 2 micron was found to work well along with a value of $d_{AC}$ less than 2 micron. Values outside this range would still work well. As the size of the microdevice decreases the optimal value of $d_{MD}$ can be less than 1 micron.

The amount of non-magnetic material separating the magnetic elements from the end of the microdevice impacts the strength of the interaction holding the microdevice on the arraying chip surface in the presence of a field along the z-axis sufficient to disarray the microdevice. These parameters along with the saturation magnetization of the magnetic elements and the shape and amount of magnetic material can be used to fine-tune the arraying process.

Adhesion.

In real fluids under non-idealized conditions adhesive forces between microdevices and between microdevices and the arraying chip can be significant ("The science of adhesive joints" by Bikerman Academic Press, NY 1961). This is especially true for high surface tension fluids such as water. The adhesive forces between surfaces are exerted perpendicular to the flat surface of the microdevices. Adhesion is due to a variety forces, including capillary, electrostatic, van der Waals, and chemical ("Critical review: Adhesion in surface micromechanical structures" by Maboudian & Howe J. Vac. Sci. Technol. B, 15:1-20 (1997)). The strength of adhesion is principally dependent on the properties of the solvent (e.g., surface tension) as well as the properties of the surface (e.g., roughness, stiffness, hydrophilicity).

While adhesive forces exist between the arraying chip surface and the microdevices, it is the adhesive force between microdevices that represents a major barrier to microdevice dissociation and arraying. This is because the arraying chip is stationary. Upon application of an appropriate magnetic field a mis-arrayed adherent microdevice can experience the full magnetic force (e.g., a lifting force) that opposes adhesion. In the case of microdevice-microdevice adhesion, the microdevices are able to move in concert in an applied magnetic field so that only a portion of the magnetic force can be applied to overcoming adhesion.

For example, first consider magnetically self-associated microdevices in a real fluid on a nonmagnetic substrate in the center of three nested Helmholtz coils. Magnetic forces drive the formation of self-associated chains and adhesive forces between microdevices support the formation of chains of microdevices. In uniform magnetic fields the same torque is applied to each microdevice. Consequently, the major force opposing infinite chain length is shear forces resulting from the interaction between the fluid and the microdevice chain. This shear force is dependent on the speed of rotation, the properties of the fluid, and the relevant surface area. For microdevices laying flat in the x-y plane and being rotated in that plane the relevant surface area is along the edge of the microdevice. For microdevices standing upright and being rotated in x-y plane that surface is the face of the microdevices. To a first approximation (ignoring the effect of surface overlap that occurs during self-assembly of microdevices) for a microdevice of the type shown in FIGS. 7, 8, and 9 (60× 75×3 micron) the shearing forces on an upright microdevice are at least 20× larger than those of a microdevice laying flat. Consequently, it is expected that rotations of upright microdevices will result in shorter chain lengths than rotations of microdevices that are laying flat.

Replacing the non-magnetic substrate in the example above with an arraying chip leads to additional forces being exerted on the magnetically-assembled microdevice chains. In the presence of a dominant arraying field, some of the microdevices will magnetically assemble with the magnetic elements of the arraying chip.

However, as occupancy increases additional repulsive forces arising from the magnetically arrayed microdevices result in a dramatic decrease in arraying efficiency—these repulsive interactions push the microdevice chains away from the surface. This is particularly true if there is a sizeable field along the z-axis. In addition, the remaining self-associated microdevices are likely to be more difficult to dissociate than the initial mixture since loosely associated microdevices are likely to be the first arrayed. The magnetic self-assembly process, as shown in eqn 5 and discussed above, is distance dependent. Consequently, in real fluids magnetic arraying in the presence of uniform magnetic fields is aided by retaining the microdevices in the x,y plane.

One method of improving arraying efficiency is to alter the solution conditions, for example by decreasing the surface tension of the liquid-surface interface. One way to accomplish this is through the use of pure organic solvents or additives to aqueous solutions such as acetonitrile, alcohols (methanol, ethanol, isopropanol, etc) or detergent. Additives such as methanol and acetonitrile also increase the viscosity of aqueous solutions resulting in greater shear forces, which will also aid in separating adhered microdevices.

Surface roughing can also be used. Surface properties can also be modulated through chemical treatments. For example, application of silanes can be used to generate hydrophilic (including charged surfaces) or hydrophobic surfaces, which will either favor or disfavor adhesion (depending on the solution conditions). Such approaches are well established in the art of surface chemistry and microfabrication. However, many surface treatments can be incompatible with certain applications; consequently it is desirable to provide a robust procedure for disruption of adhesion that will work with virtually all surfaces and chemistries.

Magnetic self-assembly increases adhesive strength since individual microdevices will not strongly associate once suspended in solution without application of a force to drive them (e.g., magnetic, fluidic, chemical (including evaporation and solvent based forces such as hydrophobicity). Similarly non-self-associated microdevices on an arraying chip surface in the presence of an arraying field will not self-associate to any appreciable extent. Consequently, since adhesive forces are a primary barrier to arraying, disruption of the adhesive force in the presence of an arraying force will significantly accelerate and enhance the arraying process.

One way to disrupt these adhesive interactions is by applying magnetic force. In the presence of a varying magnetic field gradient, such as that produced by a laboratory stir plate, the microdevices will experience a net force that will be different at different positions along the self-assembled chain. This leads to some difference in the magnetic force exerted on different microdevices in the chain and serves to facilitate disruption of adhesive interactions. A more significant aspect of rotating magnetic field gradients is that there is a lag in microdevice magnetization as the field changes. This results in different portions of the chain experiencing a different magnetic field leading to repulsive interactions between adhered microdevices. These repulsive forces are sufficient to overcome adhesive forces.

A preferred embodiment is a magnetic field generator that produces variable magnetic field gradients along the x-, y-, and z-axes. Preferably, the fields generated by this device can be adjusted such that they are insufficient to dis-array a properly arrayed microdevice, but sufficient to remove misarrayed microdevices.

For example, such a device can consist of a permanent magnet or assembly of magnets on a magnetic stir plate. The arraying chip can rest above the device. In a preferred embodiment the distance between the rotating magnet and the arraying chip is adjustable to facilitate regulation of the effective magnetic field experienced by the arraying chip. A second magnetic device (e.g. electromagnetic coil or permanent magnet) generates a fixed arraying field. In preferred embodiments the field is generated by an electromagnetic coil or a pair of coils allowing the strength of the arraying field to be adjustable. In another preferred embodiment the device produces a rotating field in the x-y plane by means of a set of small magnetic coils that can be energized in a sequence. In addition to the distance between the coil array and the arraying chip being adjustable the energy provided to the coils can be controlled to facilitate regulation of the effective magnetic field experienced by the arraying chip. Arrays of such small coils are widely used in commercially available magnetic stirrers.

A rotating field with field gradients along the x-, y-, and z-axes is also a preferred embodiment for mixing microdevices when a persistent state of self-assembly is not desired. Such situations often exist when microdevices are being used in liquid array form, since persistent chained states result in microdevice surface area being protected from interaction with the surrounding fluid. Specifically, situations where a persistent chained state is not desired can include all processing and assay steps, including microdevice surface modification, attachment of moieties, sample screening, assay development, etc.

While the magnetic energy of arraying and of assembly is always attractive when using low coercivity materials in uniform magnetic fields, in the presence of changing magnetic fields (such as rotation of a permanent magnet or reversal of the current in a magnetic coil) the magnetic force can momentarily be repulsive. This repulsive energy plays a critical role in overcoming adhesion between microdevices and facilitating the arraying process as discussed above. To a first approximation this repulsive energy can be considered to be of equal magnitude to the attractive energy and is more than sufficient to overcome the surface adhesion of microdevices.

Directing Microdevice Orientation.

Figure 12:
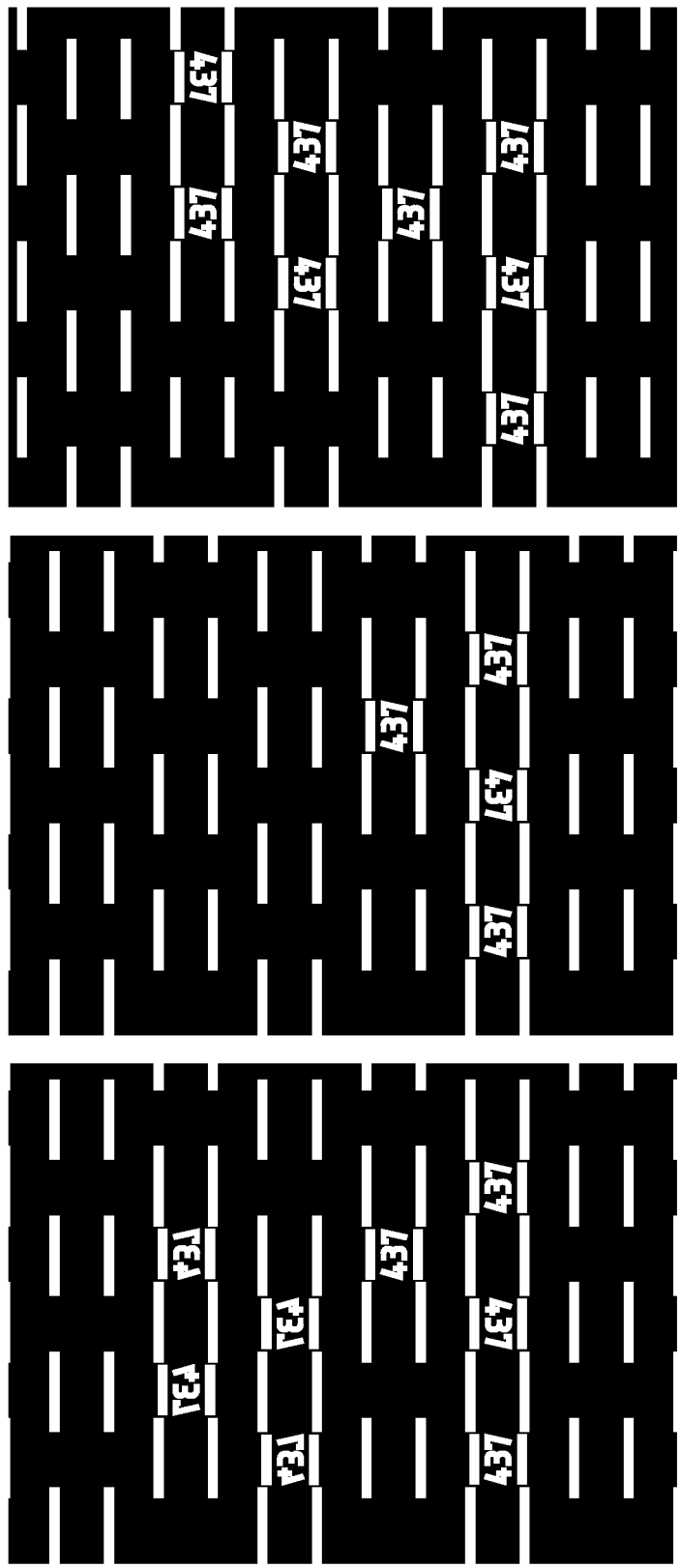
FIG. 12. Actual representation of the process of magnetic assembly of microdevices to form a "face-up" planar array. Left panel: arrayed mixture of face-up and face down microdevices; Center panel: same view during application of a lifting field that lifts only the face-down microdevices; Right panel: same view after inverting the arraying field and turning off the lifting field—all microdevices are face-up.

The use of secondary fields to drive the arraying process manifests itself clearly in the ability of at least some of the preferred embodiments to direct the sidedness of the microdevices in the assembled array. The ability to discriminate between microdevices that are face-up and face-down is achieved through an asymmetric arrangement of the magnetic elements within the microdevice. One such example of this asymmetry is asymmetry along the z-axis (the thickness of the microdevice) where there is a difference in the distance between the face-up and face-down surfaces of the microdevice and the magnetic elements within the microdevice. FIG. 9 shows examples of face-up and face-down microdevices of the same type used in arraying experiments. The sensitivity of the arraying force to the distance between magnetic poles is reflected in eqn. 2. As shown in eqn. 4 this distance is dependent on the thicknesses of the layers encapsulating the magnetic elements in the arraying chip as well as in the microdevices. Microdevices of the type shown in FIG. 9 have a thicker top layer (upside face) of silicon dioxide (1.8 micron) than bottom layer (downside face) of silicon dioxide (1.0 micron). The arraying chip shown in FIG. 10 is covered by a ~0.4 micron layer of silicon dioxide. Consequently, in their arrayed position, face-up microdevices have magnetic bars 1.4 micron away from the magnetic bars on the arraying chip, while face-down microdevices have their magnetic bars 2.2 micron away from the magnetic bars on the arraying chip. This difference in distance (1.4 vs. 2.2 micron) is sufficiently large that in the presence of an appropriate arraying field, a lifting force (e.g., magnetic, fluidic, or other) can be directed such that microdevices arrayed in a face-down position are lifted off the surface of the arraying chip and microdevices arrayed in a face-up position remain in their arrayed position. One such process of face-up arraying is shown in FIG. 12. In that process an arrayed mixture of face-up and face down microdevices are subjected to a lifting field (z-axis) that lifts only the face-down microdevices. Inverting the arraying field (by reversing the direction of the current through the arraying coils) and then turning off the lifting field results in the formerly face-down microdevices becoming face-up.

Figure 13:
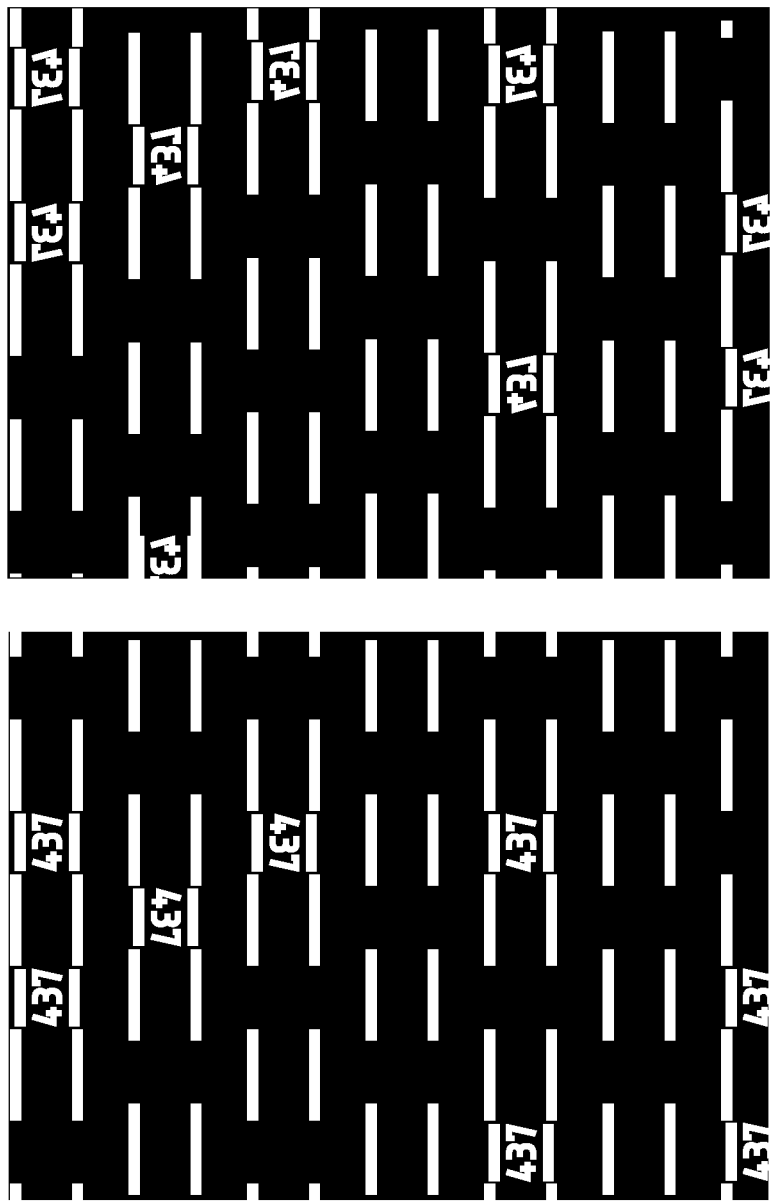
FIG. 13. Actual representation of a "face-down" planar array. Left panel: arrayed face-up microdevices; Right panel: same view after applying a lifting field, inverting the arraying field, and turning off the lifting field—all microdevices are face-down.

Moreover, if a face-down orientation is desired, once the face-up arraying process has been completed, the microdevices can be "flipped" by varying the external magnetic fields as shown in FIG. 13. In the process shown in FIG. 13 all of the microdevices are subjected to a lifting field (z-axis) that lifts them from the surface. Inverting the arraying field and then turning off the lifting field results in the formerly face-up microdevices becoming face-down. It is contemplated that differences in thickness as small as a 1% can be used to direct face-up/face-down orientation. In a preferred embodiment this difference in thickness is greater than 10%. In a further preferred embodiment this difference is greater than 50%. In a still further preferred embodiment this difference is greater than 100%.

Figure 14:
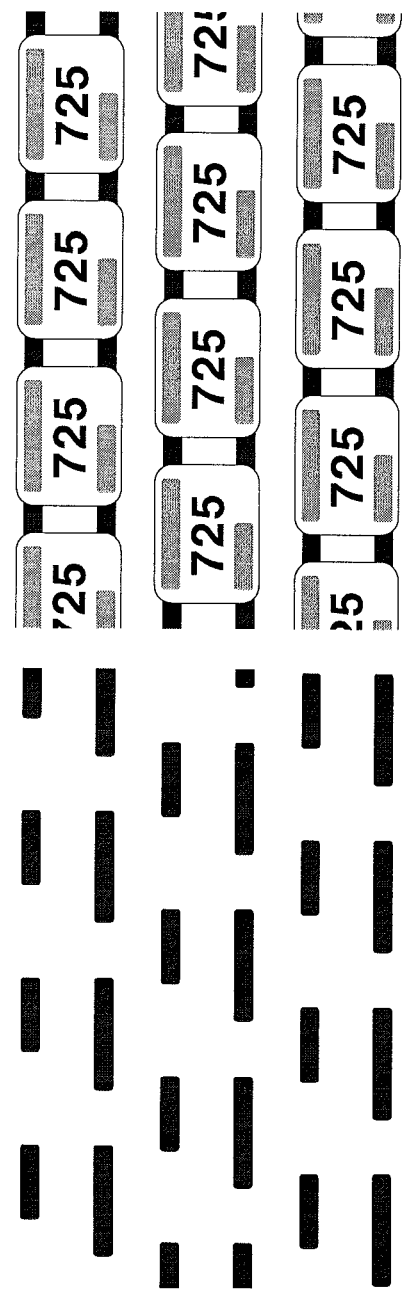
FIG. 14. Schematic representation of magnetic assembly using microdevices with magnetic elements that are located such that they are asymmetric with respect to any rotation.

The use of magnet elements that are asymmetric within the x-y-plane (face of the microdevice) can also be used to direct the orientation of microdevices. For example, microdevices of the type shown in FIG. 8 can be directed to array in one discrete orientation (dependent on the magnetic elements on the arraying chip). FIG. 14 shows a schematic representation of this arraying process. Directing the orientation of microdevices by using asymmetry within the x-y-plane can be independent of the previously described method that exploits the distance dependence of the arraying force to control sidedness, thereby allowing the two methods to be used in concert.

Figure 15:
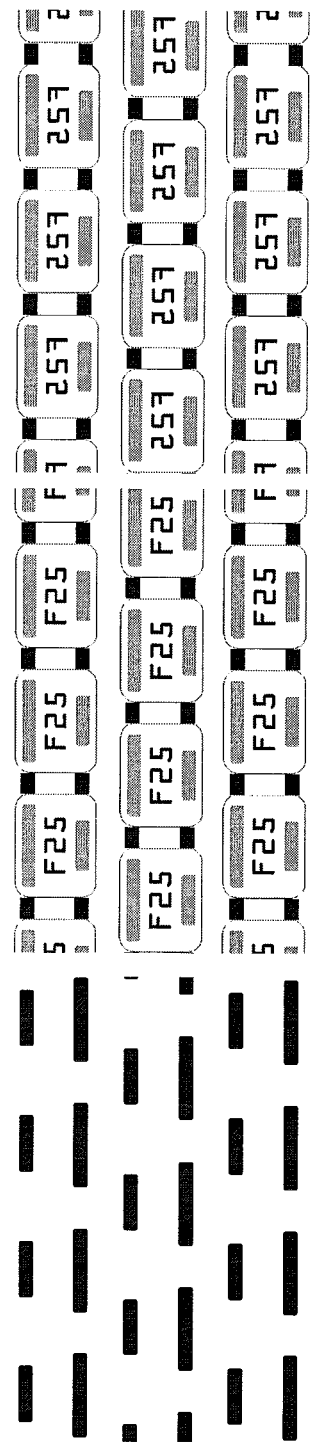
FIG. 15. Schematic representation of arrays of face-up and face-down microdevices containing magnetic elements located such that they are asymmetric with respect to any rotation in the x,y plane.
Figure 16:
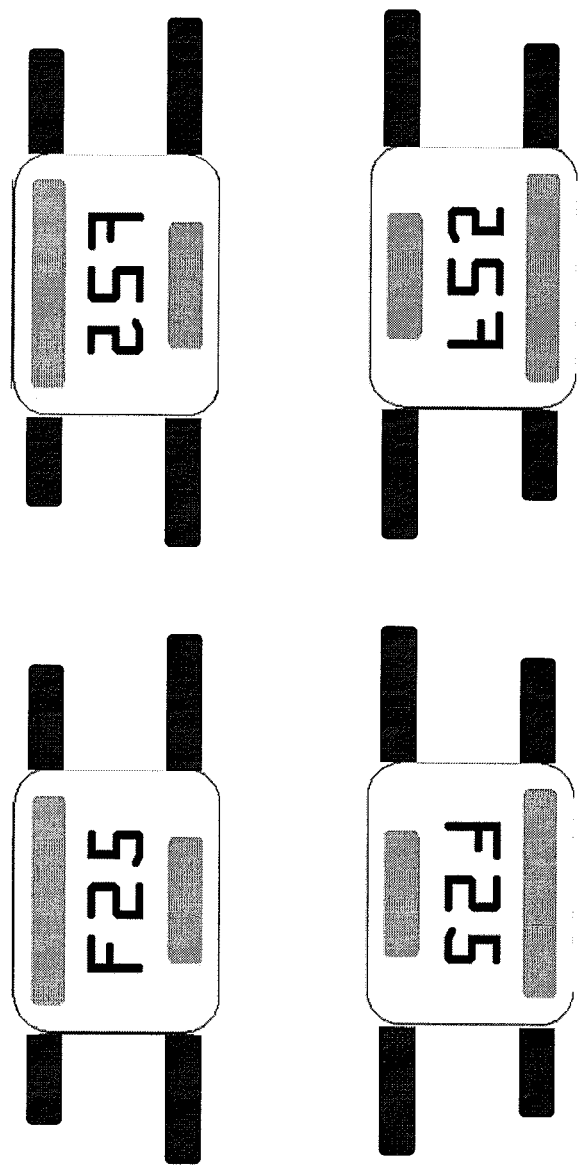
FIG. 16. Schematic representation showing four orientations of a microdevice relative to arraying elements: Upper Left—Face-up and Top-edge-up; Upper Right—Face-down and Top-edge-up; Lower Left—Face-up and Top-edge-down; Lower Right—Face-down and Top-edge-down.

There are a large number of possible discrete orientations of a microdevice in addition to face-up and face-down. As shown schematically in FIG. 14, microdevices can be oriented with respect to the x- and y-axes (width and length of the microdevice). FIG. 15 shows a schematic representation of face-up and face-down microdevices in an arrayed form. Moreover, as the magnetic elements of the microdevice are asymmetric with respect to the width and thickness of the microdevice, by appropriate choice of arraying elements they can be directed to orient in one of four orientations relative to the arraying elements as shown in FIG. 16. Magnetic elements within a microdevice as well as the arraying elements need not be parallel or perpendicular to the edges of the microdevices or the arraying chip. Consequently, any orientation of a microdevice relative to any fixed line within the plane of the arraying chip can be obtained.

Moreover, a microdevice can be oriented at different angles outside the plane of the arraying chip. Irrespective of the face-up and face-down orientation microdevices can be stood on an edge as shown in FIG. 11, the choice of edge being dictated by the direction of the external magnet field. Moreover, by varying the intensities of the magnetic field the angle of inclination of a microdevice can be varied from 0 to 90 degrees (flat to fully upright). This is demonstrated in FIG. 11, where in the center and right panels not only has the direction of the magnetic field been changed (different edge is on the surface of the arraying chip) but the strength of the lifting field (z-axis) relative to the arraying field (x-axis) has been reduced in the right panel such that microdevices are at an angle of less than 90 degrees.

The face-up/face-down ratio can also be affected by non-magnetic methods. Microdevices of the type shown in FIG. 9 that have a thicker top layer (upside face) of silicon dioxide (1.8 micron) than bottom layer (downside face) of silicon dioxide (1.0 micron) also have non-uniform densities. The magnetic bars have a density of ~9 $g/cm^3$, while silicon dioxide has a density of ~2 $g/cm^3$. This results in the microdevices being "bottom-heavy", i.e. the majority of their weight being in their lower half. As a consequence when microdevices are released into a solution and allowed to settle they preferentially land in a face-up orientation.

Figure 17:
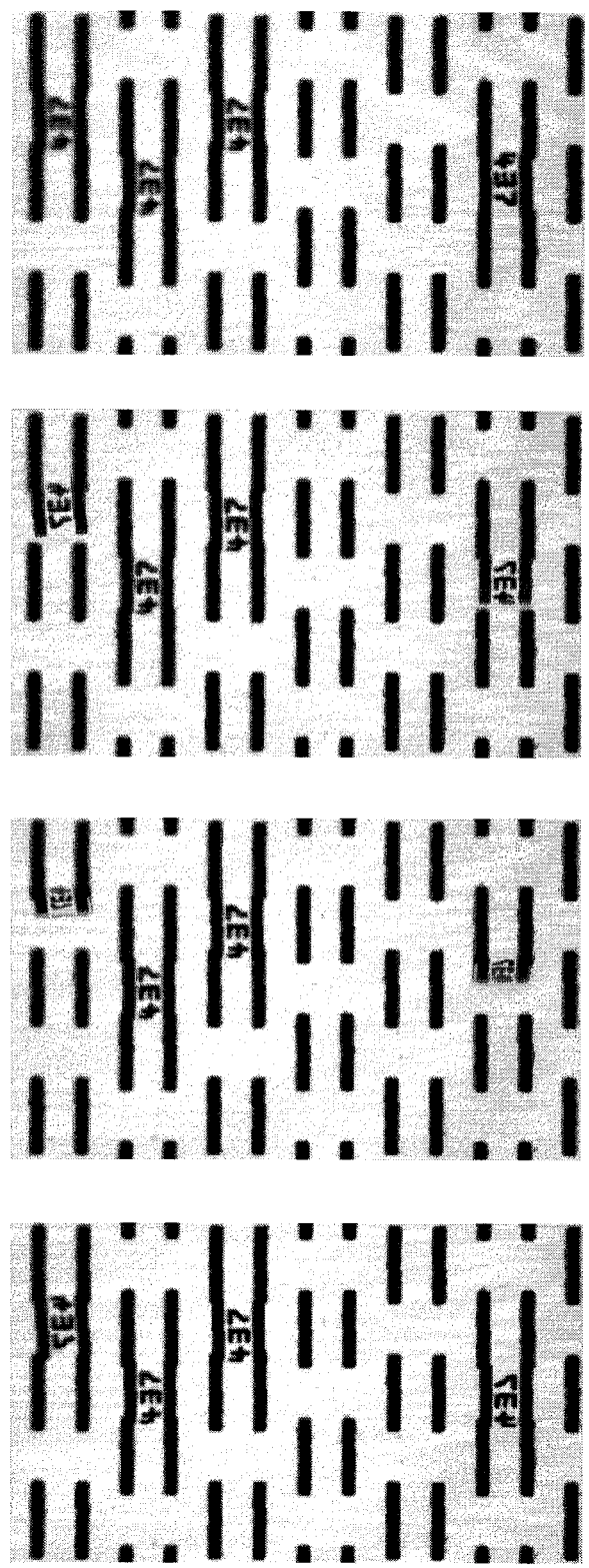
FIG. 17. Actual representation of the process of magnetic assembly of microdevices to form a "face-up" planar array by flipping in place. Left panel: arrayed mixture of face-up and face down microdevices; Center left panel: same view during application of a lifting field that lifts only the face-down microdevices; Center right panel: same view after lifting field has been reduced; Right panel: same view after inverting the arraying field and turning off the lifting field—all microdevices are face-up and in the same location on the array as they were before the flipping process.

The example of face-up/face-down arraying shown in FIGS. 12 and 13 represents only one method of manipulating the orientation of the microdevices that contain magnetic elements that are asymmetric with respect to their location along the thickness of the microdevice (z-axis). In that example, the face-up and face-down locations of the microdevices on the array are not the same as flipping has resulted in a shift of the microdevice to a position adjacent to its original position within the array. In a preferred embodiment the microdevices are flipped in place so that they occupy the same position in the array after being flipped. This can be accomplished in a number of ways. In one case a flipping-in-place process is carried out by reducing the strength of the lifting field (z-axis) prior to inversion of the arraying field (x-axis) and rather than smoothly varying the arraying field during inversion instead jumping it in steps including a step where the power supply supplying current to the arraying coils is set to zero current. FIG. 17 shows an example of microdevices that were flipped in place using this process. Flipping in place can also be facilitated by alterations in the arraying chip configuration as discussed below.

Figure 18:
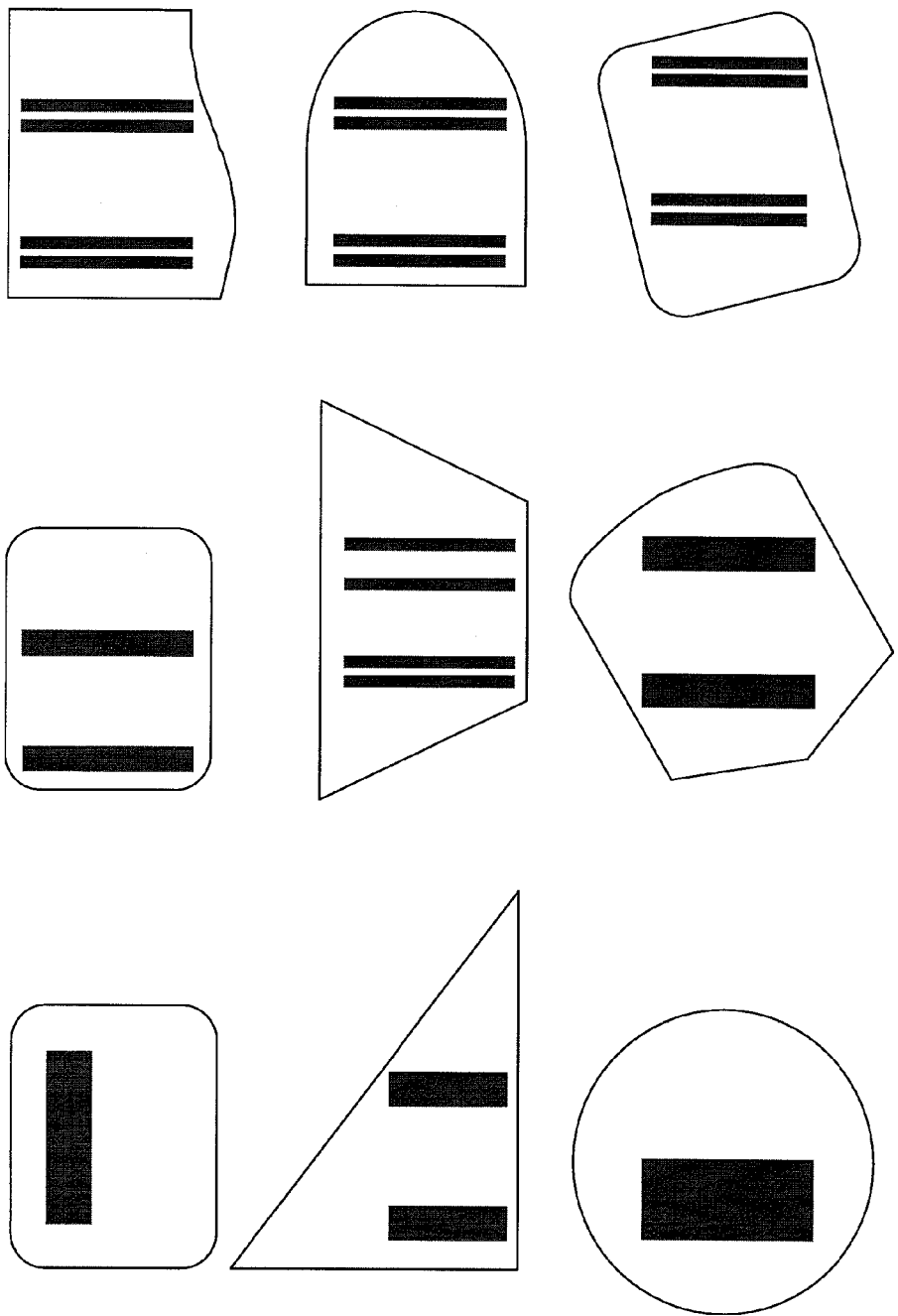
FIG. 18. Examples of asymmetric microdevices. Microdevices comprise either an asymmetrical shape or an asymmetrical arrangement of magnetic elements or both. Microdevices are asymmetrical with respect to rotation in the x,y plane.

Specific orientation of microdevices can be achieved by exploitation of differences in symmetry along any axis of the microdevice that results in their being a difference in the strength of the interaction between the microdevice and the arraying chip. Additionally, if an arraying process is carried out in a well or indentation that is complementary in shape to the microdevice then asymmetrical shaped microdevices can be used to eliminate symmetry. It is the overall symmetry of the microdevice that is at issue. Consequently, a symmetrical magnetic bar(s) and a symmetrical shape can yield an asymmetrical microdevice if none of the symmetry planes and axes of the magnetic elements and the shape are coincident. FIG. 18 shows several such asymmetric microdevices. These examples are illustrative and are in no way exhaustive.

Magnetic Complementarity.

Apart from any consideration of overall magnetic strength, the length of the bars on the arraying chip relative to the length of the bars in the microdevices can be important. Microdevices are directed into position by both attractive and repulsive forces arising from overlap or near overlap of magnetic regions between microdevices and between microdevices and the arraying chip. Preferably, the elements on the microdevices and on the arraying chip are of similar length (within a factor or two). Since the "magnetic charge" is concentrated near the ends of the magnetic regions, long bars would attract significantly shorter bars in their central region. It is important to recognize that since these interactions are weaker than the properly arrayed orientation a dislodging magnetic force could be used to disrupt them. However, when bars are of similar length the interaction between fully overlapping bars is no longer attractive, but repulsive. This repulsive interaction is exploited in the staggered configuration of arraying chip magnetic elements such as those shown in FIG. 10. Since longer magnetic regions decrease array density, shorter bars are generally preferred.

The ability of long bars to have favorable magnetic interactions when overlapping with much smaller bars can be used to create arraying chip patterns that increase the overall strength of desirable arraying interactions and improve the efficiency of arraying. In this procedure a magnetic bar of an arrayed microdevice fully overlaps a smaller bar while still engaging in favorable interactions by partially overlapping two other bars, FIG. 19 shows schematic examples of the arraying process on chips containing magnetic bars that are smaller than the magnetic bar on the microdevice to be arrayed. FIG. 20 shows an actual example of an arraying chip using this type of bar pattern. In a preferred embodiment the fully overlapped bar on the array is less than 50% of the length of the overlapping bar on the arrayed microdevice. Arraying through the use of arraying chips that use a combination of partial and complete overlap greatly facilitates flipping in place of microdevices containing a magnetic bar that is asymmetrically located along the z-axis as demonstrated in FIG. 20 that shows microdevices that are 60×70×3 micron and have a thicker top layer (upside face) of silicon dioxide (1.8 micron) than bottom layer (downside face) of silicon dioxide (1.0 micron) are flipped in place. While the process shown in FIG. 20 is very similar to one shown in FIG. 17, the addition of the small magnetic bar on the arraying chip of the type shown in FIG. 20 facilitates the flipping-in-place process and even fully upright (lifted 90 degrees to the surface of the arraying chip) microdevices can be flipped-in-place on such arraying chips. In a preferred embodiment the arraying chips contain alternating large and small bars. In a further preferred embodiment the small bars are less than 60% of the gap between the larger bars. The optimal gap spacing along the axis of arraying between sets of magnetic elements is dependent on a number of factors. These include the shape and composition of the magnetic elements (both in the microdevice and in the arraying chip) as well as the strength of the arraying field. Because the arraying process involves strong interactions between the magnetic poles the gap spacing should generally be smaller than the length of the complementary magnetic element in the microdevice. This distance can be calculated computationally using standard programs designed to calculate magnetic fields. This distance can also be measured empirically. Similarly, optimal bar size can readily be determined both computationally and empirically. A wide-range of gap and bar sizes are compatible with the arraying process and they need not correspond to the energetically most favorable dimensions.

Figure 21:
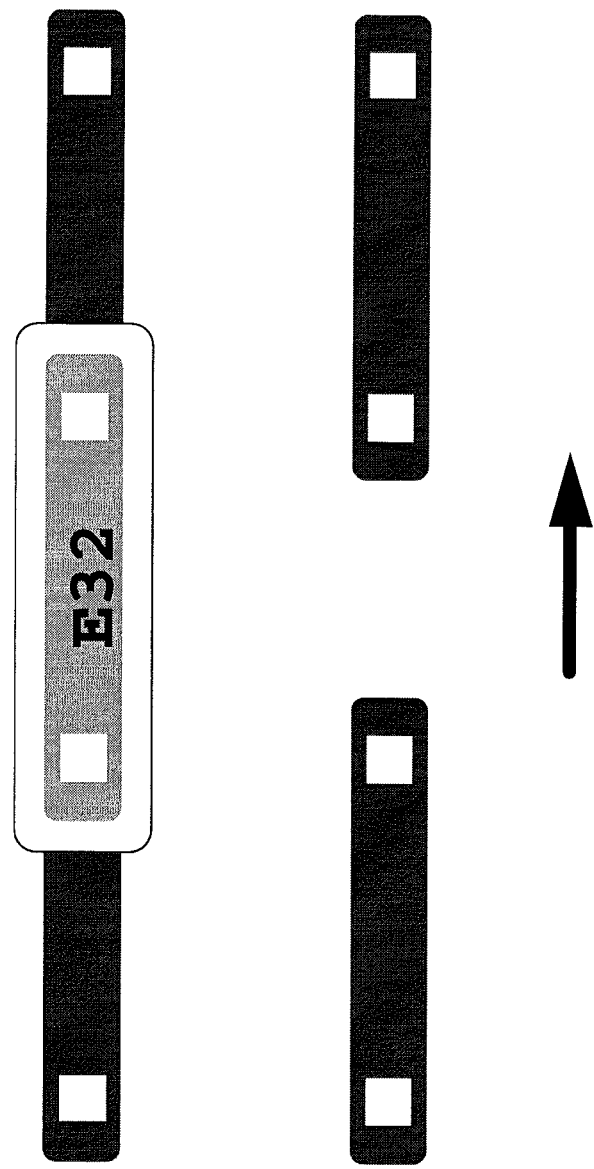
FIG. 21. Schematic representation showing alignment of a microdevice relative to arraying elements where the magnetic elements contain complementary holes: upper portion shows arrayed microdevice and lower portion shows unoccupied arraying site.
Figure 22:
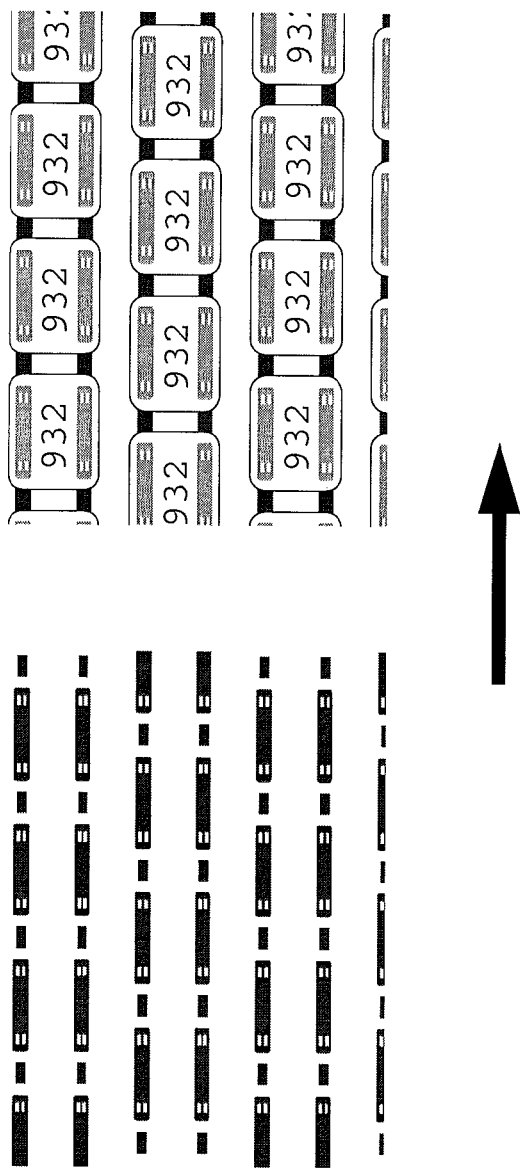
FIG. 22. Schematic representation of magnetic assembly of microdevices to form planar arrays where bars in the microdevices and the arraying chip contain complementary holes. Left panel shows a portion of an arraying chip and right panel shows arrayed microdevices on that same portion of the arraying chip FIG. 23. Actual representation of magnetic assembly of microdevices to form planar arrays shown schematically in FIG. 22, where bars in the microdevices and the arraying chip contain complementary holes. Illumination is from below showing the overlap of the holes in the microdevice and the arraying chip.
Figure 23:
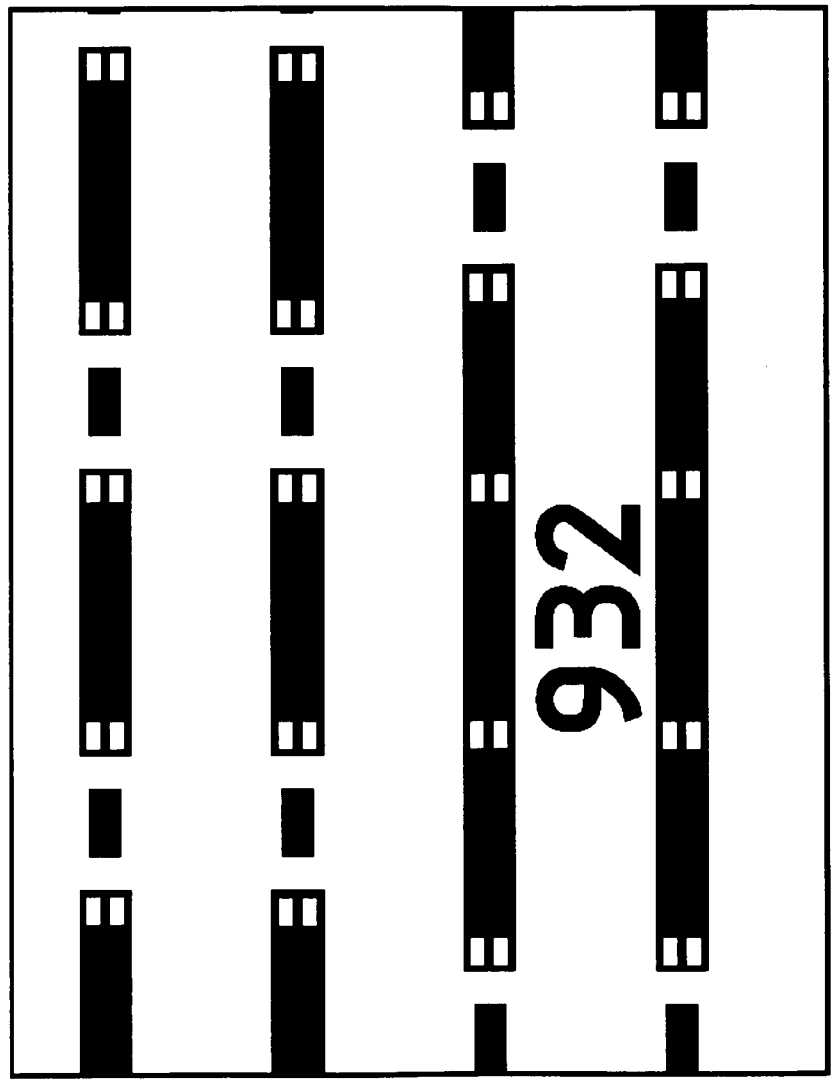
Figure 24:
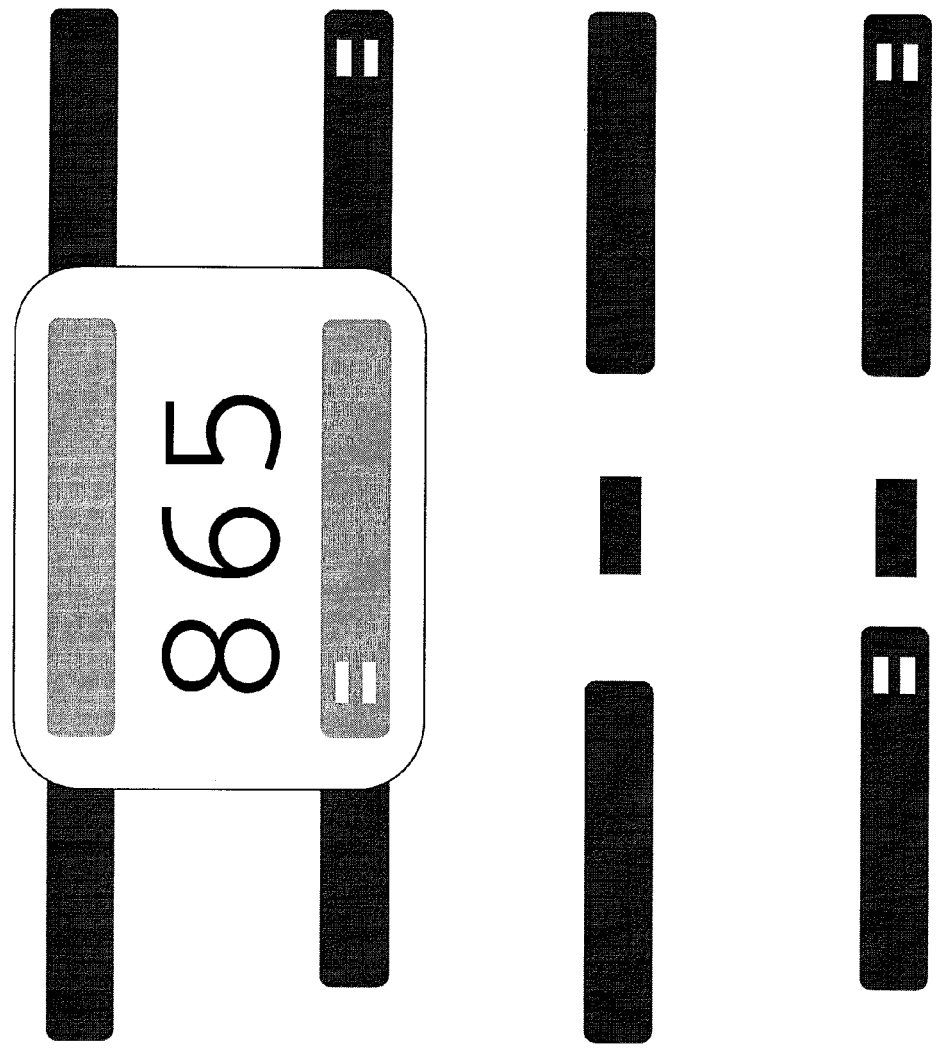
FIG. 24. Schematic representation showing alignment of a microdevice relative to arraying elements where the magnetic elements contain holes that are asymmetrically located within the microdevice: upper portion shows arrayed microdevice and lower portion shows unoccupied arraying site.
Figure 25:
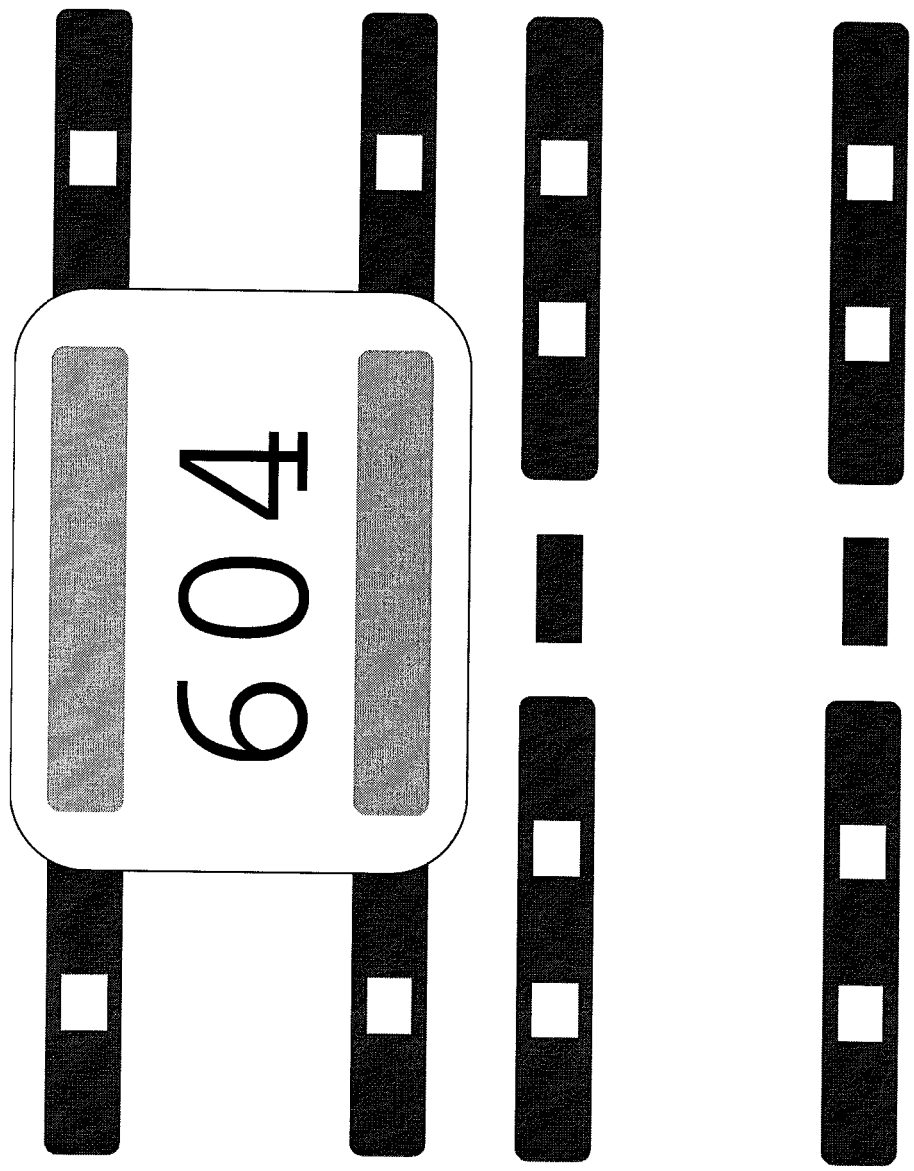
FIG. 25. Schematic representation showing alignment of a microdevice relative to arraying elements where only the magnetic elements on the arraying chip contain holes: upper portion shows arrayed microdevice and lower portion shows unoccupied arraying site.
Figure 26:
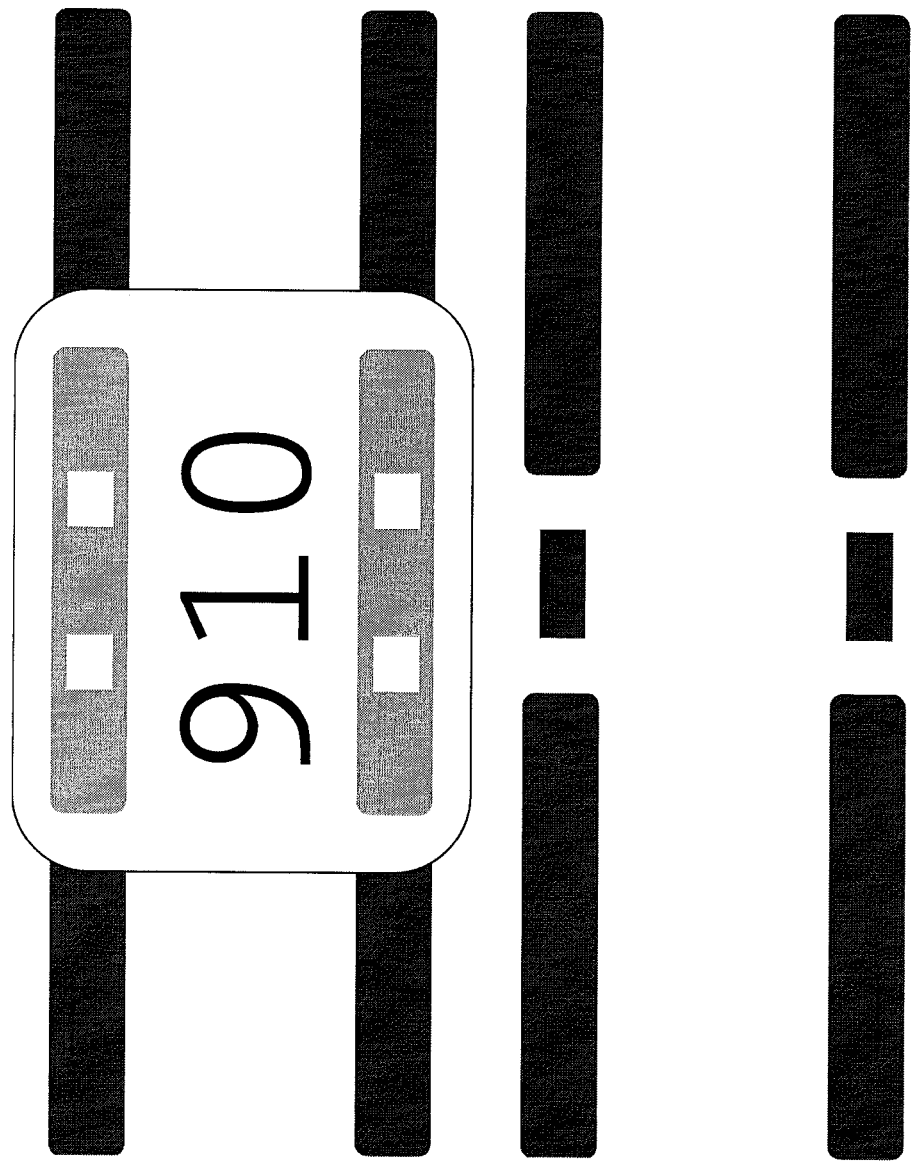
FIG. 26. Schematic representation showing alignment of a microdevice relative to arraying elements where only the magnetic elements on the microdevice contain holes: upper portion shows arrayed microdevice and lower portion shows unoccupied arraying site.

In a preferred embodiment the magnetic elements contain a hole or gap. In a magnetic field, the interaction of a magnetic material with a nonmagnetic material such as exists in a hole is weaker than the interaction between two magnetic materials. Consequently, holes can be used to direct microdevice positioning as well as to create asymmetrical bar configurations to assist in microdevice orientation. FIG. 21 shows a schematic drawing of a microdevice and a portion of an arraying chip with complementary holes. Substantial overlap of the holes leads to the energetically most stable state in a magnetic field parallel to the preferential axis of the bars on the arraying chip. FIG. 22 shows a schematic example of arrayed microdevices on an arraying chip containing a bar pattern with complementary holes and a small central bar for overlap. FIG. 23 shows an actual example of arrayed microdevices shown schematically in FIG. 22. Illumination from below demonstrates the alignment of the holes. FIG. 24 shows a schematic example of a microdevice containing a bar pattern with asymmetrically located holes arraying on a complementary set of arraying bars. It is however, not necessary that the magnetic elements in the arraying chip and in the microdevice have complementary holes. FIGS. 25 and 26 show schematic examples where holes are used to direct microdevice positioning but only the arraying chip or the microdevice (not both) has magnetic elements that contain holes.

Arraying Chip Coercivity.

The proper arrangement of magnetic elements on the arraying chip is dependent on the magnetic properties of the magnetic elements on the arraying chip and the magnetic properties of the magnetic elements of the microdevices. As discussed above a preferred embodiment for microdevices is that their magnetic elements have low coercivity and low remanence so that they will not strongly self-associate in the absence of an external magnetic field. For microdevices of this type, sorting chips containing a wide range of magnetic materials can be used. One preferred embodiment is that the magnetic elements in the sorting chips have low coercivity. To array microdevices on arraying chips with low coercivity elements, magnetic overlap is used, where the North-seeking poles overlap South-seeking poles. FIG. 3 shows a schematic example of the arraying process using low coercivity elements. The examples shown in FIGS. 4, 10, 11, 12, 13, 17, 20, and 23 correspond to this situation.

Figure 27:
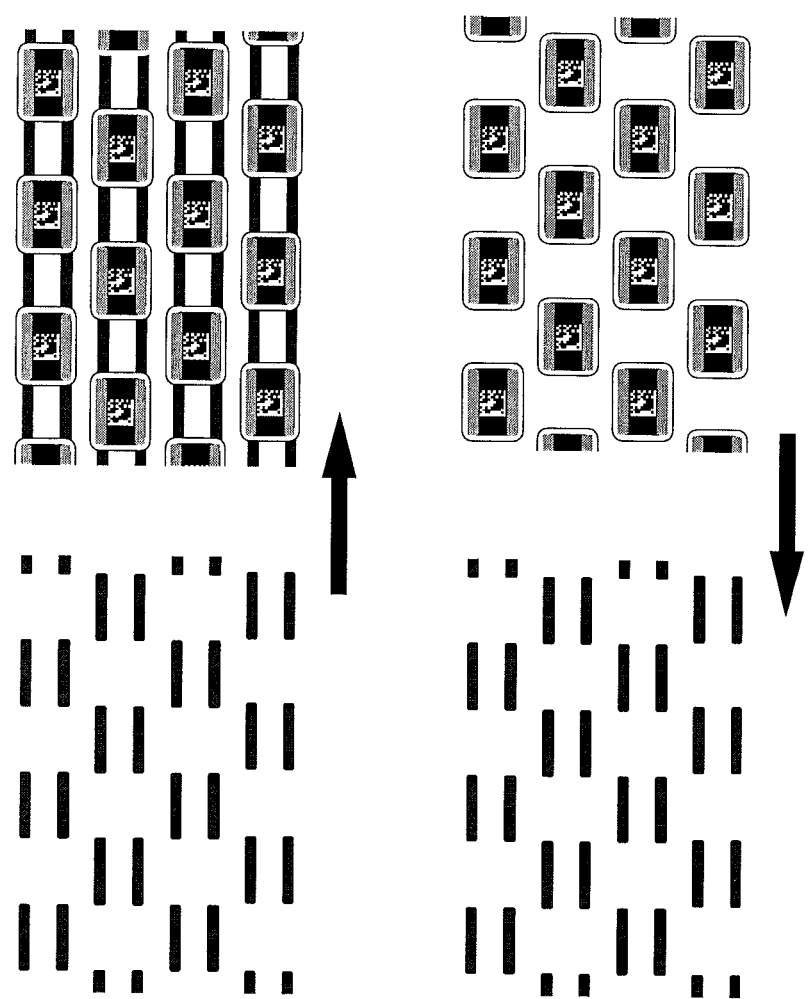
FIG. 27. Schematic representation of arraying of low coercivity microdevices on a high coercivity arraying chip. Upper panel shows microdevice arrayed when the external field is aligned in parallel with the direction of magnetization of the magnetic elements on the arraying chip. Lower panel shows microdevices arrayed when the external field is aligned in antiparallel with the direction of magnetization of the magnetic elements on the arraying chip. Arrow indicates the direction of the external magnetic field.

Another preferred embodiment is that the magnetic elements in the arraying chip have high coercivity. To array microdevices on sorting chips with high coercivity elements, magnetic overlap is used. Unlike the magnetic overlap that occurs between low coercivity magnetic elements, magnetic overlap between a low coercivity magnetic element and a high coercivity magnetic element is dependent on the specific direction of the external magnetic field. FIG. 27 shows a schematic example of a magnetic bar arrayed using such bars with the external field running parallel and anti-parallel to the direction of the magnetization of the high coercivity elements.

Figure 28:
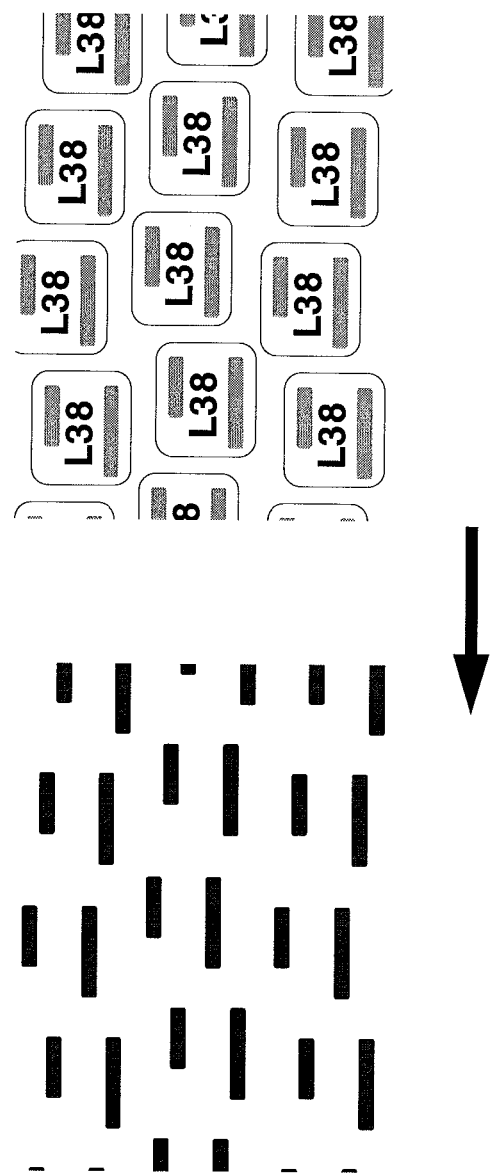
FIG. 28. Schematic representation of arraying of low coercivity microdevices on a high coercivity arraying chip, where arraying elements are arranged so as to provide no well-defined gaps between adjacent elements. Microdevices are arrayed in an external field that is aligned in antiparallel with the direction of magnetization of the magnetic elements on the arraying chip. Arrow indicates the direction of the external magnetic field.

For high coercivity arraying elements there is no need for gaps to be present in order to array. A preferred embodiment is an arrangement of magnetic elements arranged so as to provide no well-defined gaps between adjacent elements. FIG. 28 shows a schematic example of microdevices being arrayed where the microdevices and arraying chip meet these criteria.

Programmed Movements.

In a preferred embodiment the magnetic field generator is controllable such that sequences of magnetic field changes can be executed in a programmed manner (for example by means of a set of electromagnetic coils powered by digitally controllable power supplies). Much of the early discussion has focused on the microdevice behavior as the magnetic fields are changed within planes parallel and perpendicular to the preferential axis of magnetization of the arraying chip. This was done for clarity of explanation and in a preferred embodiment field gradients are altered 3-dimensionally (e.g. along x, y, and z axes). In a further preferred embodiment the direction of the arraying field is pulsed. Such pulses are preferably carried out a frequency of 1 Hz or greater. This maintains an arraying field while exerting a torque on non-arrayed microdevices. In other preferred embodiments fields along the non-arraying axes (e.g. y and z) are varied (field direction and/or amplitude) in the presence of an arraying field (pulsed or steady). Such programmed field variations can be used to spread microdevices over the surface of the arraying chip by magnetic means as well as direct microdevices into an arrayed state. For example, by pulsing the direction of the magnetic fields along all three axes, microdevices can be spread over the surface of the arraying chip and by setting the y field to zero at fixed intervals while increasing the z-field at those same fixed intervals the microdevices can be directed towards arraying sites in a lifted form (e.g. as shown in the center panel of FIG. 11). The z-field can then be set to zero driving the lifted microdevice into an arrayed state (e.g. as shown in the center and right panel of FIG. 12). The process can be repeated to drive any non-arrayed microdevices into an arrayed state. Such cycles can be carried out in less than 1 second. Many other types of programmed movement of microdevices are possible. For example, microdevices can be directed to "walk" along the arraying chip parallel to the preferential axis of magnetization of the arraying chip. Such a walking motion is analogous to the type of motion shown in FIG. 12 where the lifted microdevices are flipped into an adjacent arraying site, but in the walking motion the lifting field is not removed so that the microdevice stays upright when moved into the adjacent site. The process can be repeated so as to direct the microdevices to walk from one end of the arraying chip to the other if so desired.

Library Synthesis

Arraying offers significant advantages in the area of library synthesis and screening. Libraries can be produced by synthesizing compounds directly onto the microdevices. Solid phase synthesis methods are widely used and microdevice surface chemistry can be constructed so as to be compatible with existing solid phase protocols. The most widely utilized technique to make a particle-based library is "split-and-mix" synthesis in which mixtures of beads are split randomly prior to the start of each synthetic cycle and pooled at the completion of the cycle, the process is continued for as many cycles as desired. Ideally this results in each bead containing only a single compound (ignoring at this point contributions from incomplete coupling steps). However, the specific compounds contained in split-and-mix libraries can not be determined unless the libraries generated are "fully combinatorial", meaning that the library contains all possible combinations of building blocks (e.g. amino acids, nucleotides, etc). Since such combinatorial libraries are extremely large in practice the actual composition of the random library is not known. By arraying before and/or after each split and mix step and keeping track of the identities of the microdevices through identification of their coding patterns the precise composition of the random library can be determined. In addition such information allows the identity of the compound on each encoded microdevice to be known facilitating the screening process. An additional advantage of arraying the microdevices at each step in the synthetic process is that in addition to the identity of the microdevice a measure of the coupling efficiency of that synthetic step on each individual microdevice can be determined through the use of nondestructive assays (e.g. colorometric or fluorogenic). For example in the case of peptide synthesis, there are established assays that can be used to determine the completion of coupling at the level of individual beads ("The one-bead-one-compound combinatorial method" by Lam et al. Chem. Rev. 97:411-448 (1997)). However, in a random bead library since it is not feasible using current bead encoding technologies to routinely decode the entire library this information is of limited utility; determining that the efficiency of a coupling step was greater than 95% on 95% of the beads does not determine the level or purity or the composition of the major side products on any individual bead. Such particle specific information is of great importance when interpreting results obtained from researching (e.g. screening for function or activity) the library. For example, a group of microdevices containing very different main products could contain significant amounts of similar side products due to incomplete reactions occurring at various steps in the synthesis. By tracking this information at every step in the synthesis the distribution of side products can be recorded. The ability of the microdevice to contain sensors or other types of MEMS devices offers additional advantages in researching the library by allowing the microdevices to serve as both the substrate for synthesis as well as the analysis device.

It should be apparent to those skilled in the art that many more modifications besides those already described are possible without departing from the inventive concepts herein. Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps could be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A magnetic arraying device, comprising:
   an arraying chip comprising a substrate having embedded magnetizable magnetic elements forming an array of discrete regions, wherein each element exerts magnetic forces as induced by an external magnetic field, and wherein the magnetic elements comprise alternating longer and shorter magnetic bars;
   wherein the shorter bars are each positioned in a gap between the ends of adjacent longer bars along the long axis of the longer bars, at least some of the longer bars having an average length of less than 500 µM, and at least some of the shorter bars having an average length of less than 50% of the longest bars; and
   an arrayed plurality of microdevices placed upon the arraying chip, wherein at least some of the microdevices comprise a magnetic bar having a length greater than the gap between ends of adjacent long bars in the arraying chip, wherein the microdevices are configured to be moved on the substrate by a field created by the longer bars and shorter bars, and wherein at least some of the microdevices further comprise at least one of a chemically active site, a magnetic coding space, mutually distinct polymers, or mutually distinct codes.

2. The device of claim 1, wherein the longer and shorter bars alternate in a long-short-long-short fashion.

3. The device of claim 1, wherein the longer and shorter bars alternate in other than a long-short-long-short fashion.

4. The device of claim 1, further comprising a gap between ends of adjacent longer bars, and wherein the length of the shorter bars is less than 60% of the gap.

5. The device of claim 1, wherein at least one of the plurality of microdevices has a chemically active site.

6. The device of claim 5, wherein the chemically active site is suitable for attachment of a chemical moiety.

7. The device of claim 5, wherein the chemically active site is suitable for attachment of a biological moiety.

8. The device of claim 1, wherein the magnetic bar of at least one of the plurality of microdevices is disposed off-center in the at least one of the plurality of microdevices.

9. The device of claim 1, wherein an induced magnetization in its absolute magnitude along an element preferential axis of magnetization of each element of the arraying chip is at least more than 20% than an induced magnetization of the element along at least one other axis.

10. The device of claim 9, wherein an induced magnetization in its absolute magnitude along an element preferential axis of magnetization of each of the plurality of microdevices is at least more than 20% than an induced magnetization of the microdevice along at least one other axis.

11. The device of claim 1, wherein an orientation of the microdevices can be directed to at least two discrete orientations of the microdevices.

12. The device of claim 1, wherein an orientation of the microdevices can be directed to at least eight discrete orientations of the microdevices.

13. The device of claim 1, wherein an orientation of the microdevices can be directed to at least twelve discrete orientations of the microdevices.

14. The device of claim 1, wherein each of the plurality of microdevices has a longest linear dimension of 500 microns.

15. The device of claim 1, wherein each of the plurality of microdevices completely overlaps a magnetizable magnetic element of the arraying chip.

16. The device of claim 1, wherein the arrayed plurality of microdevices comprise a patterned magnetic bar.

17. The device of claim 1, wherein selected ones of the plurality of microdevices are configured to re-orient by at least 90 degrees when a first magnetic field and a second magnetic field are sequentially applied to the arraying chip.

18. The device of claim 17, wherein the selected ones of the plurality of microdevices are flipped upside down.

19. The device of claim 17, wherein the selected ones of the plurality of microdevices are flipped upside down without changing their locations with respect to the arraying chip.

20. The device of claim 1, wherein at least one of the plurality of microdevices includes a magnetic coding space that supports at least $10^3$ choices.

21. The device of claim 1, wherein each of the plurality of microdevices includes mutually distinct polymers.

22. The device of claim 1, wherein each of the plurality of microdevices includes mutually distinct codes.

* * * * *